United States Patent
Canning et al.

(10) Patent No.: US 10,960,080 B2
(45) Date of Patent: Mar. 30, 2021

(54) PEGYLATED PORCINE INTERFERON AND METHODS OF USE THEREOF

(71) Applicants: ELANCO US INC., Greenfield, IN (US); AMBRX, INC., La Jolla, CA (US)

(72) Inventors: Peter Connor Canning, Indianapolis, IN (US); Nickolas Knudsen, Escondido, CA (US); Lillian Skidmore, San Diego, CA (US)

(73) Assignees: Elanco US Inc., Greenfield, IN (US); Ambrx, Inc., La Jolla, CA (US)

(*) Notice: Subject to any disclaimer, the term of this patent is extended or adjusted under 35 U.S.C. 154(b) by 4 days.

(21) Appl. No.: 16/311,540

(22) PCT Filed: Jun. 16, 2017

(86) PCT No.: PCT/US2017/037964
§ 371 (c)(1),
(2) Date: Dec. 19, 2018

(87) PCT Pub. No.: WO2017/222940
PCT Pub. Date: Dec. 28, 2017

(65) Prior Publication Data
US 2019/0192673 A1    Jun. 27, 2019

Related U.S. Application Data

(60) Provisional application No. 62/352,163, filed on Jun. 20, 2016.

(51) Int. Cl.
| | |
|---|---|
| A61K 47/60 | (2017.01) |
| C07K 14/56 | (2006.01) |
| A61P 31/14 | (2006.01) |
| A61K 9/00 | (2006.01) |
| A61K 47/02 | (2006.01) |
| A61K 47/10 | (2017.01) |
| A61K 47/12 | (2006.01) |
| A61K 38/00 | (2006.01) |

(52) U.S. Cl.
CPC ............ *A61K 47/60* (2017.08); *A61K 9/0019* (2013.01); *A61K 47/02* (2013.01); *A61K 47/10* (2013.01); *A61K 47/12* (2013.01); *A61P 31/14* (2018.01); *C07K 14/56* (2013.01); *A61K 38/00* (2013.01)

(58) Field of Classification Search
None
See application file for complete search history.

(56) References Cited

U.S. PATENT DOCUMENTS

| | | |
|---|---|---|
| 2007/0237743 A1 | 10/2007 | Villarete et al. |
| 2008/0132681 A1 | 6/2008 | Hays et al. |

FOREIGN PATENT DOCUMENTS

| | | |
|---|---|---|
| CN | 104262480 | 1/2015 |

OTHER PUBLICATIONS

Fernandez-SainZ et al., 2015, Virology, vol. 483, p. 284-290. (Year: 2015).*
Brockmeier et al., 2016, Swine Health, p. 1-9. (Year: 2016).*
F Lefevre et al: "Molecular cloning and sequencing of a gene encoding biologically active porcine alpha-interferon", J. Interferon Res., vol. 6, No. 4, Aug. 1, 1986, pp. 349-360, XP055396551.
International Search Report and Written Opinion issued by the International Searching Authority in PCT/US2017/037964, dated Aug. 17, 2017, 11 pages.

* cited by examiner

*Primary Examiner* — Gary B Nickol
*Assistant Examiner* — Jegatheesan Seharaseyon
(74) *Attorney, Agent, or Firm* — Perry Woo

(57) ABSTRACT

Disclosed herein are porcine interferon alpha variants (pIFN-α) comprising a synthetic amino acid at select locations in pIFN-α and a one or two amino acid insertion in the N-terminus after removal of the signal peptide. The pIFN-α variants can further be pegylated. Methods of making and administering these compounds to treat virus infections in pigs and formulations comprising the variants are also provided.

14 Claims, 5 Drawing Sheets

Figure 1:
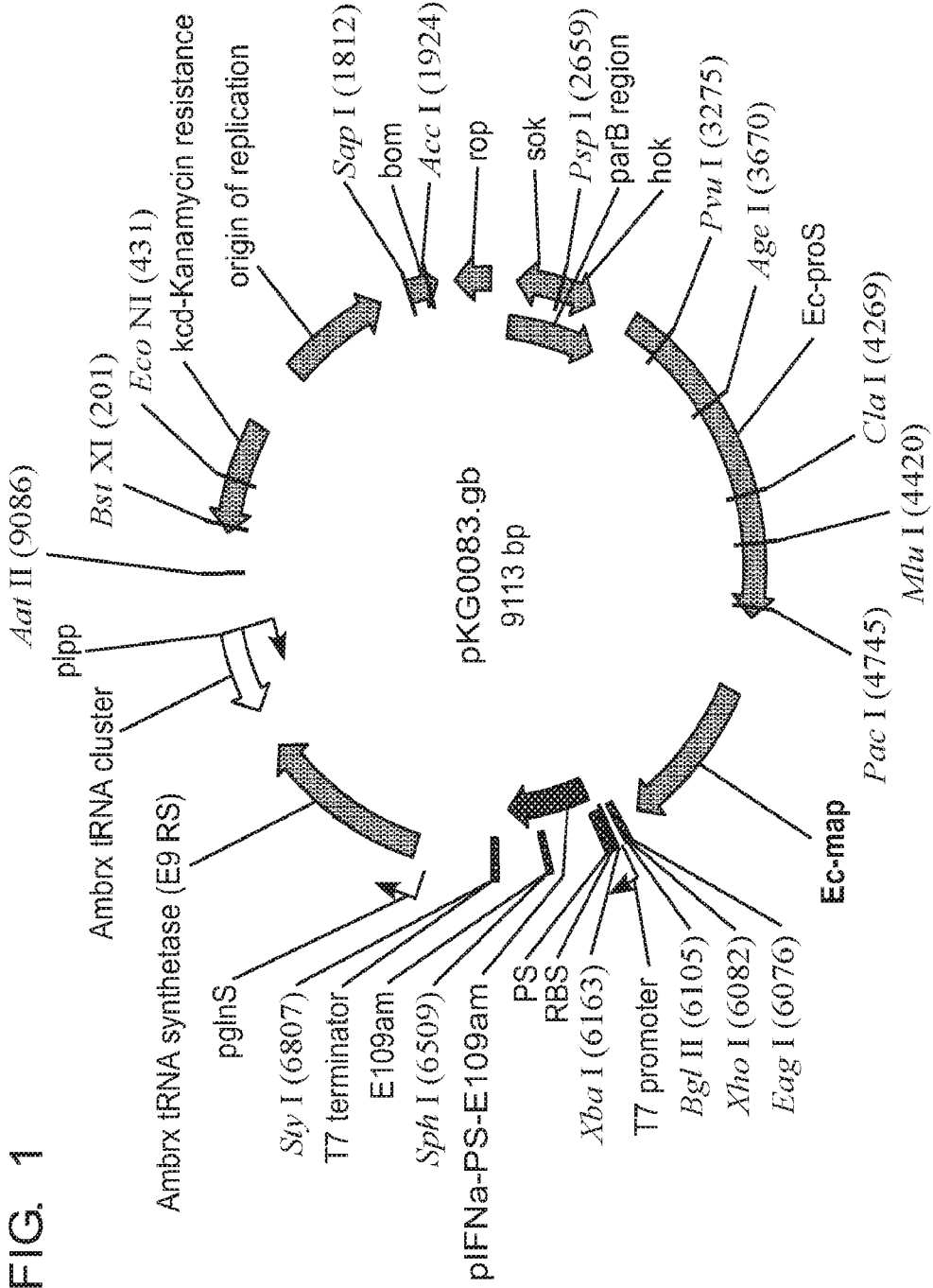

Specification includes a Sequence Listing.

| pAF site | Sequence | SEQ ID NO: | X= |
|---|---|---|---|
| Q102 | CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMXEAGLEGTPLLEEDSIRAVRKYFHRLTLYLQEKSYSPCAWEIVRAEVMRSFSSSRNLQDRLRKKE | 6 | 102 |
| Q102 | PCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMXEAGLEGTPLLEEDSIRAVRKYFHRLTLYLQEKSYSPCAWEIVRAEVMRSFSSSRNLQDRLRKKE | 7 | 103 |
| Q102 | PSCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMXEAGLEGTPLLEEDSIRAVRKYFHRLTLYLQEKSYSPCAWEIVRAEVMRSFSSSRNLQDRLRKKE | 8 | 104 |
| E103 | CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQXAGLEGTPLLEEDSIRAVRKYFHRLTLYLQEKSYSPCAWEIVRAEVMRSFSSSRNLQDRLRKKE | 9 | 103 |
| E103 | PCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQXAGLEGTPLLEEDSIRAVRKYFHRLTLYLQEKSYSPCAWEIVRAEVMRSFSSSRNLQDRLRKKE | 10 | 104 |
| E103 | PSCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQXAGLEGTPLLEEDSIRAVRKYFHRLTLYLQEKSYSPCAWEIVRAEVMRSFSSSRNLQDRLRKKE | 11 | 105 |
| E107 | CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLXGTPLLEEDSIRAVRKYFHRLTLYLQEKSYSPCAWEIVRAEVMRSFSSSRNLQDRLRKKE | 12 | 107 |
| E107 | PCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLXGTPLLEEDSIRAVRKYFHRLTLYLQEKSYSPCAWEIVRAEVMRSFSSSRNLQDRLRKKE | 13 | 108 |
| E107 | PSCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLXGTPLLEEDSIRAVRKYFHRLTLYLQEKSYSPCAWEIVRAEVMRSFSSSRNLQDRLRKKE | 14 | 109 |
| L112 | CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLXEEDSIRAVRKYFHRLTLYLQEKSYSPCAWEIVRAEVMRSFSSSRNLQDRLRKKE | 15 | 112 |
| L112 | PCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLXEEDSIRAVRKYFHRLTLYLQEKSYSPCAWEIVRAEVMRSFSSSRNLQDRLRKKE | 16 | 113 |
| L112 | PSCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLXEEDSIRAVRKYFHRLTLYLQEKSYSPCAWEIVRAEVMRSFSSSRNLQDRLRKKE | 17 | 114 |
| Y136 | CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSXSPCAWEIVRAEVMRSFSSSRNLQDRLRKKE | 18 | 136 |
| Y136 | PCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSXSPCAWEIVRAEVMRSFSSSRNLQDRLRKKE | 19 | 137 |
| Y136 | PSCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSXSPCAWEIVRAEVMRSFSSSRNLQDRLRKKE | 20 | 138 |

FIG. 2

FIG. 3

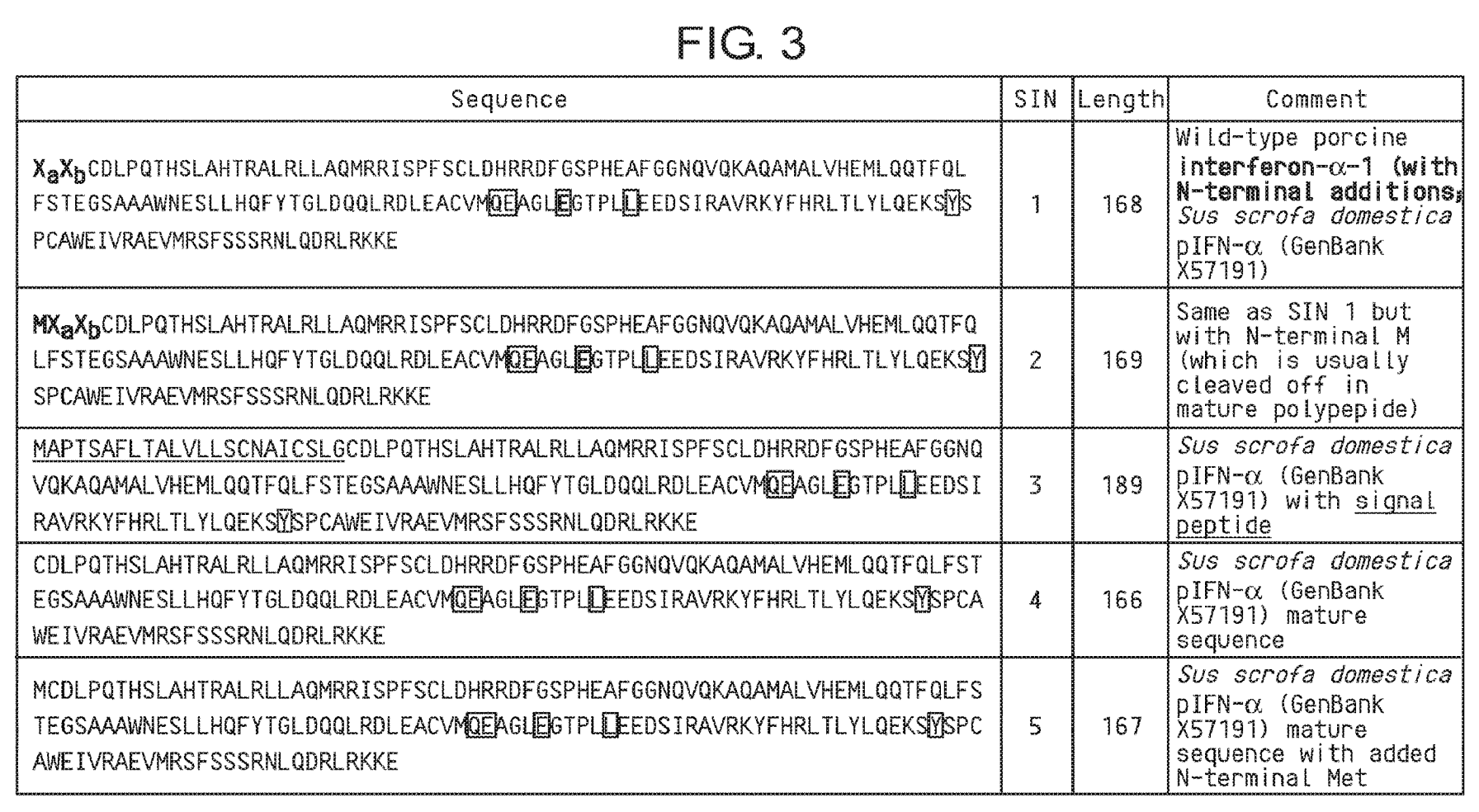

| Sequence | SIN | Length | Comment |
|---|---|---|---|
| $X_aX_b$CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSYSPCAWEIVRAEVMRSFSSSRNLQDRLRKKE | 1 | 168 | Wild-type porcine interferon-α-1 (with N-terminal additions; *Sus scrofa domestica* pIFN-α (GenBank X57191) |
| M$X_aX_b$CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSYSPCAWEIVRAEVMRSFSSSRNLQDRLRKKE | 2 | 169 | Same as SIN 1 but with N-terminal M (which is usually cleaved off in mature polypepide) |
| MAPTSAFLTALVLLSCNAICSLGCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSYSPCAWEIVRAEVMRSFSSSRNLQDRLRKKE | 3 | 189 | *Sus scrofa domestica* pIFN-α (GenBank X57191) with signal peptide |
| CDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSYSPCAWEIVRAEVMRSFSSSRNLQDRLRKKE | 4 | 166 | *Sus scrofa domestica* pIFN-α (GenBank X57191) mature sequence |
| MCDLPQTHSLAHTRALRLLAQMRRISPFSCLDHRRDFGSPHEAFGGNQVQKAQAMALVHEMLQQTFQLFSTEGSAAAWNESLLHQFYTGLDQQLRDLEACVMQEAGLEGTPLLEEDSIRAVRKYFHRLTLYLQEKSYSPCAWEIVRAEVMRSFSSSRNLQDRLRKKE | 5 | 167 | *Sus scrofa domestica* pIFN-α (GenBank X57191) mature sequence with added N-terminal Met |

FIG. 4

| $X_a$ | $X_b$ | pAF site | Sequence | SIN | Length | X= |
|---|---|---|---|---|---|---|
| abs | abs | Q102 | CDLPQTHSLAHTRALRLLAQMRRISPFSCLDHRRDFGSPHEAFGGNQVQKAQAMALVHEMLQQTFQLFSTEGSAAAWNESLLHQF YTGLDQQLRDLEACVMXE AGLEGTPLLEEDSIRAVRKYFHRLTLYLQEKSYSPCAWEIVRAEVMRSFSSSRNLQDRLRKKE | 6 | 166 | 102 |
| abs | Pro | Q102 | PCDLPQTHSLAHTRALRLLAQMRRISPFSCLDHRRDFGSPHEAFGGNQVQKAQAMALVHEMLQQTFQLFSTEGSAAAWNESLLHQ FYTGLDQQLRDLEACVMXEAGLEGTPLLEEDSIRAVRKYFHRLTLYLQEKSYSPCAWEIVRAEVMRSFSSSRNLQDRLRKKE | 7 | 167 | 103 |
| Pro | Ser | Q102 | PSCDLPQTHSLAHTRALRLLAQMRRISPFSCLDHRRDFGSPHEAFGGNQVQKAQAMALVHEMLQQTFQLFSTEGSAAAWNESLLH QFYTGLDQQLRDLEACVMXEAGLEGTPLLEEDSIRAVRKYFHRLTLYLQEKSYSPCAWEIVRAEVMRSFSSSRNLQDRLRKKE | 8 | 168 | 104 |
| abs | abs | E103 | CDLPQTHSLAHTRALRLLAQMRRISPFSCLDHRRDFGSPHEAFGGNQVQKAQAMALVHEMLQQTFQLFSTEGSAAAWNESLLHQF YTGLDQQLRDLEACVMQXAGLEGTPLLEEDSIRAVRKYFHRLTLYLQEKSYSPCAWEIVRAEVMRSFSSSRNLQDRLRKKE | 9 | 166 | 103 |
| abs | Pro | E103 | PCDLPQTHSLAHTRALRLLAQMRRISPFSCLDHRRDFGSPHEAFGGNQVQKAQAMALVHEMLQQTFQLFSTEGSAAAWNESLLHQ FYTGLDQQLRDLEACVMQXAGLEGTPLLEEDSIRAVRKYFHRLTLYLQEKSYSPCAWEIVRAEVMRSFSSSRNLQDRLRKKE | 10 | 167 | 104 |
| Pro | Ser | E103 | PSCDLPQTHSLAHTRALRLLAQMRRISPFSCLDHRRDFGSPHEAFGGNQVQKAQAMALVHEMLQQTFQLFSTEGSAAAWNESLLH QFYTGLDQQLRDLEACVMQXAGLEGTPLLEEDSIRAVRKYFHRLTLYLQEKSYSPCAWEIVRAEVMRSFSSSRNLQDRLRKKE | 11 | 168 | 105 |
| abs | abs | E107 | CDLPQTHSLAHTRALRLLAQMRRISPFSCLDHRRDFGSPHEAFGGNQVQKAQAMALVHEMLQQTFQLFSTEGSAAAWNESLLHQF YTGLDQQLRDLEACVMQEAGLXGTPLLEEDSIRAVRKYFHRLTLYLQEKSYSPCAWEIVRAEVMRSFSSSRNLQDRLRKKE | 12 | 166 | 107 |
| abs | Pro | E107 | PCDLPQTHSLAHTRALRLLAQMRRISPFSCLDHRRDFGSPHEAFGGNQVQKAQAMALVHEMLQQTFQLFSTEGSAAAWNESLLHQ FYTGLDQQLRDLEACVMQEAGLXGTPLLEEDSIRAVRKYFHRLTLYLQEKSYSPCAWEIVRAEVMRSFSSSRNLQDRLRKKE | 13 | 167 | 108 |
| Pro | Ser | E107 | PSCDLPQTHSLAHTRALRLLAQMRRISPFSCLDHRRDFGSPHEAFGGNQVQKAQAMALVHEMLQQTFQLFSTEGSAAAWNESLLH QFYTGLDQQLRDLEACVMQEAGLXGTPLLEEDSIRAVRKYFHRLTLYLQEKSYSPCAWEIVRAEVMRSFSSSRNLQDRLRKKE | 14 | 168 | 109 |
| abs | abs | L112 | CDLPQTHSLAHTRALRLLAQMRRISPFSCLDHRRDFGSPHEAFGGNQVQKAQAMALVHEMLQQTFQLFSTEGSAAAWNESLLHQF YTGLDQQLRDLEACVMQEAGLEGTPLXEEDSIRAVRKYFHRLTLYLQEKSYSPCAWEIVRAEVMRSFSSSRNLQDRLRKKE | 15 | 166 | 112 |
| abs | Pro | L112 | PCDLPQTHSLAHTRALRLLAQMRRISPFSCLDHRRDFGSPHEAFGGNQVQKAQAMALVHEMLQQTFQLFSTEGSAAAWNESLLHQ FYTGLDQQLRDLEACVMQEAGLEGTPLXEEDSIRAVRKYFHRLTLYLQEKSYSPCAWEIVRAEVMRSFSSSRNLQDRLRKKE | 16 | 167 | 113 |
| Pro | Ser | L112 | PSCDLPQTHSLAHTRALRLLAQMRRISPFSCLDHRRDFGSPHEAFGGNQVQKAQAMALVHEMLQQTFQLFSTEGSAAAWNESLLH QFYTGLDQQLRDLEACVMQEAGLEGTPLXEEDSIRAVRKYFHRLTLYLQEKSYSPCAWEIVRAEVMRSFSSSRNLQDRLRKKE | 17 | 168 | 114 |
| abs | abs | Y136 | CDLPQTHSLAHTRALRLLAQMRRISPFSCLDHRRDFGSPHEAFGGNQVQKAQAMALVHEMLQQTFQLFSTEGSAAAWNESLLHQF YTGLDQQLRDLEACVMQEAGLEGTPLLEEDSIRAVRKYFHRLTLYLQEKSXSPCAWEIVRAEVMRSFSSSRNLQDRLRKKE | 18 | 166 | 136 |
| abs | Pro | Y136 | PCDLPQTHSLAHTRALRLLAQMRRISPFSCLDHRRDFGSPHEAFGGNQVQKAQAMALVHEMLQQTFQLFSTEGSAAAWNESLLHQ FYTGLDQQLRDLEACVMQEAGLEGTPLLEEDSIRAVRKYFHRLTLYLQEKSXSPCAWEIVRAEVMRSFSSSRNLQDRLRKKE | 19 | 167 | 137 |
| Pro | Ser | Y136 | PSCDLPQTHSLAHTRALRLLAQMRRISPFSCLDHRRDFGSPHEAFGGNQVQKAQAMALVHEMLQQTFQLFSTEGSAAAWNESLLH QFYTGLDQQLRDLEACVMQEAGLEGTPLLEEDSIRAVRKYFHRLTLYLQEKSXSPCAWEIVRAEVMRSFSSSRNLQDRLRKKE | 20 | 168 | 138 |

$X_a X_b$ CDLPQTHSLAHTRALRLLAQMRRISPFSCLDHRRDFGSPHEAFGGNQVQKAQAMALVHEMLQQTFQLFSTEGSAAAWNESLLHQFYTGLDQQL RDLEACVMQEAGLXEGTPLXEEDSIRAVRKYFHRLTLYLQEKSXSPCAWEIVRAEVMRSFSSSRNLQDRLRKKE       (SEQ ID NO: 1)

166 residue sequence "WT pIFN-alpha"
```
  1 CDLPQTHSLA HTRALRLLAQ MRRISPFSCL DHRRDFGSPH EAFGGNQVQK AQAMALVHEM LQQTFQLFST EGSAAAWNES
 81 LLHQFYTGLD QQLRDLEACV MQEAGLEGTP LLEEDSIRAV RKYFHRLTLY LQEKSYSPCA WEIVRAEVMR SFSSSRNLQD
161 RLRKKE
```

| $X_a$ | $X_b$ | pAF site | Sequence | SIN | Length | X= |
|---|---|---|---|---|---|---|
| *abs* | *abs* | H7 | CDLPQTXSLAHTRALRLLAQMRRISPFSCLDHRRDFGSPHEAFGGNQVQKAQAMALVHEMLQQTFQLFS<br>TEGSAAAWNESLLHQFYTGLDQQLRDLEACVMQEAGLEGTPLLEEDSIRAVRKYFHRLTLYLQEKSYSP<br>CAWEIVRAEVMRSFSSSRNLQDRLRKKE | 21 | 166 | 7 |
| *abs* | *abs* | R34 | CDLPQTHSLAHTRALRLLAQMRRISPFSCLDHRXDFGSPHEAFGGNQVQKAQAMALVHEMLQQTFQLFS<br>TEGSAAAWNESLLHQFYTGLDQQLRDLEACVMQEAGLEGTPLLEEDSIRAVRKYFHRLTLYLQEKSYSP<br>CAWEIVRAEVMRSFSSSRNLQDRLRKKE | 22 | 166 | 34 |
| *abs* | *abs* | H40 | CDLPQTHSLAHTRALRLLAQMRRISPFSCLDHRRDFGSPXEAFGGNQVQKAQAMALVHEMLQQTFQLFS<br>TEGSAAAWNESLLHQFYTGLDQQLRDLEACVMQEAGLEGTPLLEEDSIRAVRKYFHRLTLYLQEKSYSP<br>CAWEIVRAEVMRSFSSSRNLQDRLRKKE | 23 | 166 | 40 |

FIG. 5

| $X_s$ | $X_b$ | pAF site | Sequence | SIN | Length | X= |
|---|---|---|---|---|---|---|
| *absent* | Ser | E107 | SCDLPQTHSLAHTRALRLLAQMRRISPFSCLDHRRDFGSPHEAFGGNQVQKAQAMALVHEMLQQTFQLF<br>STEGSAAAWNESLLHQFYTGLDQQLRDLEACVMQEAGLXGTPLLEEDSIRAVRKYFHRLTLYLQEKSYS<br>PCAWEIVRAEVMRSFSSSRNLQDRLRKKE | 24 | 167 | 108 |
| Ser | Gly | E107 | SGCDLPQTHSLAHTRALRLLAQMRRISPFSCLDHRRDFGSPHEAFGGNQVQKAQAMALVHEMLQQTFQL<br>FSTEGSAAAWNESLLHQFYTGLDQQLRDLEACVMQEAGLXGTPLLEEDSIRAVRKYFHRLTLYLQEKSY<br>SPCAWEIVRAEVMRSFSSSRNLQDRLRKKE | 25 | 168 | 109 |
| *absent* | His | E107 | HCDLPQTHSLAHTRALRLLAQMRRISPFSCLDHRRDFGSPHEAFGGNQVQKAQAMALVHEMLQQTFQLF<br>STEGSAAAWNESLLHQFYTGLDQQLRDLEACVMQEAGLXGTPLLEEDSIRAVRKYFHRLTLYLQEKSYS<br>PCAWEIVRAEVMRSFSSSRNLQDRLRKKE | 26 | 167 | 108 |

FIG. 6

PEGYLATED PORCINE INTERFERON AND METHODS OF USE THEREOF

CROSS-REFERENCE TO RELATED APPLICATIONS

This application is filed under 37 C.F.R. 371 as a U.S. National Phase application of, and claims the benefit of priority to, International Patent application serial number PCT/US2017/037964, filed Jun. 16, 2017, which claims the benefit of priority to U.S. Provisional Patent application Ser. No. 62/352,163, filed Jun. 20, 2016. The entire text of the aforementioned applications is incorporated herein by reference in its entirety.

The instant application contains a Sequence Listing which has been submitted in ASCII format via EFS-Web and is hereby incorporated by reference in its entirety. Said ASCII copy, created on Jun. 17, 2016 is named 204257_0028_539107_SL_ST25.txt and is 45,240 bytes in size.

Administering interferon alpha (IFN-α) has medical sequelae that need to be assessed and managed. For example, autoimmunity can also be induced by IFN-α therapy for chronic viral hepatitis in humans. Therefore, generally human treatment has been limited to patients in need of therapy, as therapy can aggravate pre-existing autoimmunity, unmask silent autoimmune processes, or even induce de novo autoimmune diseases. F. L. Dumoulin et al., "Autoimmunity induced by interferon-α therapy for chronic viral hepatitis," *Biomed. & Pharmacother.*, 53: 242-54 (1999). Interferon-α also been observed to fail to treat Hepatitis C virus infections in humans.

Interferon has been seen to be effective to treat some humans with hepatitis C virus (HCV), to the extent that two pegylated forms of interferon alpha (IFN-α) now are in clinical use for humans, i.e. Peginterferon-α-2a and Peginterferon-α-2b, known also as PEGASYS® and PEGINTRON® respectively. Yet, it remains unclear how IFN-α inhibits HCV replication. More interestingly, Peginterferon-α-2a and Peginterferon-α-2b have only 7% and 28% activity respectively as compared to their native (wild-type) forms.

In the process of making interferon, various variants have been created for human treatment to extend bioavailability and assist in protein production. One example is in U.S. Pat. No. 8,106,160, which discusses addition of one or more amino acid residues to the N-terminal cysteine of mature human interferon alpha-2b to reduce the formation of non-natural disulfide bonds and thereby lowering the level of structural isoforms. This includes the addition of a proline residue at the N-terminus.

Methods for introducing non-natural amino acids inserted into sites in a protein are described for example in WO2010/011735 and in WO2005/074650.

The wild-type porcine interferon alpha-1 is 189 amino acids in length and is located at GenBank X57191

Forms of interferon-α for use in animals and in animal husbandry are needed, especially in treating pig populations susceptible to viral infections, and even more particularly in treating pig populations with active and on-going viral infections to protect pig herds from pathology associated with viral infection. A benefit would be finding an IFN-α variant for use in porcine animals that is long acting and useful to inhibit or reduce viral replication, herd pathology and animal death related to virus infection. The porcine IFN-α variant would maintain bioactivity, have a longer bioavailability and have few isoforms allowing for easier purification.

FIG. 1 depicts plasmid pKG0083 with pIFN-α-PS-E107amber, which includes a proline-serine N-terminal insertion. This plasmid directs production of the protein variant of SEQ ID NO: 14 by the AXID2820 cell line.

FIG. 2 depicts the sequence alignments and sequence identifiers for pIFN-α variants having the synthetic amino acid pAF substituted for residues Q102, E103, E107, L112, and Y136. The sequences all lack the signal sequence for pIFN-α. The sequences either lack (SEQ ID NOS: 6, 9, 12, 15, and 18) an additional amino acid at the N-terminus, or have proline (SEQ ID NOS: 7, 10, 13, 16, and 19) or proline-serine added at the N-terminus (SEQ ID NOS: 8, 11, 14, 17, and 20).

FIG. 3 depicts the motif sequence of SEQ ID NO: 1. SEQ ID NO: 2 is the same as SEQ ID NO: 1, but includes an N-terminal methionine, which is usually cleaved in maturation of the mature pIFN-α variant. SEQ ID NO: 3 includes the signal sequence but lacks the insertion of Proline, Proline-Serine, and/or Methionine. SEQ ID NO: 4 is the wild type mature pIFN-α. SEQ ID NO: 5 is the wild-type sequence with methionine at the N-terminus.

FIG. 4 depicts in a table the various pIFN-α variants of Q102, E103, E107, L112, and 136 either having no additional residue or having a proline or proline-serine added at the N-terminus, as indicated in positions $X_a$ and $X_b$. By "abs" is meant absent. SEQ ID NO: 1 is shown for reference.

FIG. 5 depicts the sequence alignments for three additional pIFN-α variants, wherein a pAF is substituted at H7, R34, and H40. These sequences do not have either proline or proline-serine at the N-terminus, nor do they have an N-terminal methionine. The sites of mutation on depicted by boxes in the WT pIFN-alpha sequence above the table, and in the table they are depicted by a boxed "X". $X_a$ and $X_b$ are as defined in the chart. By "abs" is meant absent.

FIG. 6 depicts additional E107 mutations synthesized wherein a serine (SEQ ID NO: 24), a serine-glycine (SEQ ID NO: 25), and a histidine (SEQ ID NO: 26) are added at the amino terminus of a pIFN-α variant having pAF substituted at E107 (represented by the boxed "X"). $X_a$ and $X_b$ are as defined in the chart. By "abs" is meant absent.

Provided here are porcine interferon-α (pIFN-α) variants and methods of use thereof that can be used in animals that are not vaccinated, such as unvaccinated newborn piglets as well as in immune suppressed animals, i.e. pregnant pigs (pregnant sows or gilts); in animals where vaccination confers insufficient protection; in animals susceptible to infection by a virus for which no effective vaccine is available; and in currently-infected animals. These compositions and methods of use will be to prevent infection in the fact of a viral outbreak. The compositions can also be used to reduce the severity of disease in an infected pig. Generally, a single dosage regimen is administered. Alternatively, and as needed, dosages can be provided approximately 1-3, or 2 weeks apart, with optimally only one to two dosages administered The wild type porcine interferon-α (pIFN-α) which includes the 23 residue signal sequence is:

(SEQ ID NO: 3)
maptsaflta lvllscnaic slgcdlpqth slahtralrl laqmrrispf scldhrrdfg spheafggnq vqkaqamalv -continued
hemlqqtfql fstegsaaaw nesllhqfct gldqqlrdle acvmqeagle gtplleedsi lavrkyfhrl tlylqeksys pcaweivrae vmrsfsssrn lqdrlrkke.

The double underlined portion is the signal sequence which is not present in the mature form of wild type pIFN-α.

Provided here is a (pIFN-α) variant. The variant omits the 23 amino acid signal sequence. The variant can have a methionine residue at the amino terminal end which may be cleaved off in the mature form of the protein. This methionine is not present in the wild-type form of pIFN-α. The pIFN-α variant further has a one or two amino acid insertion between a signal sequence methionine and the N-terminal cysteine. The insertion is either a proline or a proline-serine. The sequence is depicted below:

```
                                           (SEQ ID NO: 2)
MXaXbCDLPQTHSLAHTRALRLLAQMRRISPFSCLDHRRDFGSPHEAFGG

NQVQKAQAMALVHEMLQQTFQLFSTEGSAAAWNESLLHQFYTGLDQQLRD

LEACVMQEAGLEGTPLLEEDSIRAVRKYFHRLTLYLQEKSYSPCAWEIVR

AEVMRSFSSSRNLQDRLRKKE.
```

"$X_b$" (position 3 in SEQ ID NO: 2) is either Proline, Serine or Absent. $X_a$ (position 2 in SEQ ID NO: 2) is either absent or proline. When $X_b$ is absent, $X_a$ is absent, when $X_b$ is proline $X_a$ is absent, and when $X_b$ is serine, $X_a$ is proline. The bold glutamic acid residue "E" located downstream of $X_a$ and $X_b$ is the site of substitution of a synthetic amino acid, i.e. pAF.

The pIFN-α variant further has the synthetic amino acid, para-acetyl-phenylalanine (pAF), substituted in one of 5 locations in SEQ ID NO: 1: residue E103 (SEQ ID NOS: 9 to 11 respectively), E107 (SEQ ID NOS: 12 to 14 respectively), L112 (SEQ ID NOS: 15 to 17 respectively), Y136 (SEQ ID NOS: 18 to 20), or Q102 (SEQ ID NOS: 6 to 8 respectively) (numbering is with respect to the sequence shown in SEQ ID NO: 4 without an N-terminal Met).

The pIFN-α variant can further be pegylated on the pAF. The pIFN-α variant can be pegylated with about a 5 to about a 40 kDa PEG, or with a 30 kDa PEG. The pIFN-α variant can be pegylated with a linear 30 kDa oxyamino-PEG. An activated oxyamino group reacts chemoselectively with an acetyl side chain present on a synthetic amino acid, such as para-acetylphenyalanine. A pIFN-α variant has a linear 30 kDa PEG covalently bonded to the pAF substituted at E107 (SEQ ID NOS: 12 to 14) (numbering is with respect to mature sequence shown in SEQ ID NO: 4). The E107 pIFN-α variant can further have a proline or proline and serine at the N-terminus as reflected in SEQ ID NOS: 13 and 14 respectively.

The pIFN-α variants can be incorporated into formulations. A formulation comprising the pIFN-α variants can comprise 20 mM sodium acetate, 100 mM sodium chloride, 5% glycerol at pH 5.0 of 2.0 to 6.0 g/L titer of porcine INF-α.

The formulations can be made by a method comprising the steps of:

(a) purifying the pIFN-α;
(b) solubilizing said purified pIFN-α variant in 50 mM Tris, 6M guanidine at pH 8;
(c) incubating the solubilized pIFN-αA variant at room temperature for 16-24 hours in 20 mM Tris, 1M arginine, 10 mM methionine (met), 1 mM EDTA (ethylenediaminetetraacetic acid) at pH 8.0 to allow for refolding of the protein;
(d) removing residual acetylated variants by chromatographic resolution on a strong anion exchange resin;
(e) conjugating the pIFN-α variant with PEG at a ratio of PEG to protein of between 1:1 and 1:8 or between 1:1 and 1:2; and
(f) purifying the pegylated pIFN-α variant.

The pIFN-α variants and formulations thereof can be used to treat a virus infection. A method of treating a virus infection in a pig comprising administering the pIFN-α variant subcutaneously to a pig in the amount of 25 μg/kg to 150 μg/kg animal weight of any of the porcine interferon-α (pIFN-α) variants. The method can further comprise a second administration of about 25 μg/kg to about 150 μg/kg animal weight of the pIFN-α variant. If the method involves a second administration, the second administration can occur about 7, 14, or 21 days after the first administration.

The method of treating virus infection can be used to treat a virus infection selected from the group consisting of: porcine reproductive and respiratory disease virus, foot and mouth disease virus, swine influenza virus, porcine circovirus, porcine epidemic diarrhea virus, and transmissible gastroenteritis virus. The method can be used to treat a newborn pig or a pregnant pig.

Also contemplated is a use of any of the pIFN-α variants (or a formulation containing the variant) in a therapy in a pig to treat a virus infection, wherein the infection can be caused by any of the viruses discussed herein.

Also described is a use of the pIFN-α variant for use in the manufacture of a medicament for treating a viral infection in a pig. The pig can be a newborn pig or a pregnant pig.

By "administering" is meant the injection of a therapeutically effective amount of the compounds and compositions containing said compounds disclosed. Administration can be intramuscular (i.m) or subcutaneous (s.c.). The amount of pIFN-α variant administered would be given based on the weight of the animal, for example with pregnant pigs receiving more than newborn pigs.

The formulations disclosed herein can also be placed in a single dose or a multi-dose vial.

The pig being treated by the methods described herein would be a newborn pig, r a pregnant pig (pregnant gilt or sow).

By "treat", "treating", or "treatment" is meant the reduction or amelioration of one or more symptoms associated with infection by one of the viruses mentioned herein. The composition can further be used in the manufacture of a medicament for treating a viral infection in a pig. The composition or medicament can be used to treat a pig. The pig can be a newborn pig or a pregnant pig.

Reference will now be made in detail to the compounds, formulations of said compounds, methods of making the formulations, and methods of using the compounds and formulations to treat pigs (porcines or swine) having a viral infection.

As used herein and in the appended claims, the singular forms "a," "an," and "the" include plural reference unless the context clearly indicates otherwise, and plural usage in turn can also encompass usage in the singular.

A "synthetic amino acid" refers to an amino acid that is not one of the 20 common amino acids or pyrrolysine or selenocysteine. Examples of such synthetic amino acids include, but are not limited to, para-acetyl phenylalanine (pAF), acetylglucosaminyl-L-serine, and N-acetylglucosaminyl-L-threonine. For additional details on such synthetic amino acids and their incorporation and modification, see WO2010/011735 and in WO2005/074650.

The term "subject" as used herein, refers to a pig, especially the domestic pig (*Sus scrofa domesticus* or *Sus domesticus*) and can include miniature pigs as well as those breeds raised for meat production. By "pig", "swine" or "porcine" is meant to include all pig breeds.

The term "effective amount" as used refers to that amount of the pIFN-α variant being administered which will prevent, treat, or reduce the transmission of a porcine virus from an infected animal to an uninfected animal or will prevent, treat, or reduce a symptom of a disease caused by infection with a porcine virus. Disclosed here are porcine interferon alpha (pIFN-α) variants (pIFN-α). These variants have had synthetic amino acids substituted at various positions on a porcine IFN-α sequence. A *Sus scrofa domestica* pIFN-α gene (GenBank X57191) wherein the underlined leader sequence (residues 1-23 of SEQ ID NO: 3) is removed as depicted below (amino to carboxy terminus orientation):

(SEQ ID NO: 3)
MAPTSAFLTALVLLSCNAICSLGCDLPQTHSLAHTRALRLLAQMRRISPF

SCLDHRRDFGSPHEAFGGNQVQKAQAMALVHEMLQQTFQLFSTEGSAAAW

NESLLHQFYTGLDQQLRDLEACVMQEAGLEGTPLLEEDSIRAVRKYFHRL

TLYLQEKSYSPCAWEIVRAEVMRSFSSSRNLQDRLRKKE.

The mature sequence is:

(SEQ ID NO: 4)
CDLPQTHSLAHTRALRLLAQMRRISPFSCLDHRRDFGSPHEAFGGNQVQK

AQAMALVHEMLQQTFQLFSTEGSAAAWNESLLHQFYTGLDQQLRDLEACV

MQEAGLEGTPLLEEDSIRAVRKYFHRLTLYLQEKSYSPCAWEIVRAEVMR

SFSSSRNLQDRLRKKE.

The underlined signal sequence at the N-terminus of SEQ ID NO: 3 can be replaced by another signal sequence or even with a single methionine residue, for example for in vitro transcription, resulting in the following sequence:

(SEQ ID NO: 5)
MCDLPQTHSLAHTRALRLLAQMRRISPFSCLDHRRDFGSPHEAFGGNQVQ

KAQAMALVHEMLQQTFQLFSTEGSAAAWNESLLHQFYTGLDQQLRDLEAC

VMQEAGLEGTPLLEEDSIRAVRKYFHRLTLYLQEKSYSPCAWEIVRAEVM

RSFSSSRNLQDRLRKKE or can include the proline or proline-serine residues between the N-terminal methionine and cysteine (see SEQ ID NO: 2). Other related porcine sequences can be used.

The pIFN-α variants have had synthetic amino acids introduced into one of the following locations on *Sus scrofa domestica* (using its numbering with respect to the mature sequence shown in SEQ ID NO: 4): Q102 (SEQ ID NO: 6), E103 (SEQ ID NO: 9), E107 (SEQ ID NO: 12), L112 (SEQ ID NO: 15), and Y136 (SEQ ID NO: 18) (which are bolded and underlined above) and also depicted in FIGS. 2-4. The mature pIFN-α may have the N-terminal methionine residue (e.g., residue 1 of SEQ ID NO: 5) cleaved off upon maturation.

Synthetic amino acids and their incorporation are as discussed for example in WO2010/011735. Synthetic amino acids can be used in *Escherichia coli* (*E. coli*) (e.g., L. Wang, et al., (2001), *Science* 292: 498-500) and in the eukaryote *Saccharomyces cerevisiae* (*S. cerevisiae*) (e.g., J. Chin et al., *Science* 301: 964-7 (2003)), which has enabled the incorporation of synthetic amino acids into proteins in vivo.

Of the five (5) listed synthetic amino acid substitution variants having biological activity (substitutions of pAF at one of the five E103, E107, L112, Y136, or Q102 residues of which are underlined in the sequence below), these variants can be further modified by having amino acids inserted at the N-terminus of the molecule. For example, a proline (Pro) or Proline-Serine (Pro-Ser) can be inserted between the N-terminal Met and Cys.

The mature form of the variants would omit the N-terminal methionine.

Methods of making a pIFN-α polypeptide linked to a water soluble polymer are described here. By "pegylating" and "pegylated" is meant to refer to the covalent bonding of the specified synthetic amino acid to a polyethylene glycol (PEG) molecule. The method can comprise contacting an isolated pIFN-α polypeptide comprising a synthetic amino acid with a water soluble polymer comprising a moiety that reacts with the synthetic amino acid.

The poly(ethylene glycol) molecule can have a molecular weight of between about 0.1 kDa and about 100 kDa. The poly(ethylene glycol) molecule can have a molecular weight of between 0.1 kDa and 50 kDa, 20 kDa and 40 kDa, and any integer value between 25 kDa and 35 kDa. The poly(ethylene glycol) molecule can have a molecular weight of about 30 kDa. The poly(ethylene glycol) molecule can be a linear molecule having a molecular weight of between 0.1 kDa and 50 kDa, 20 kDa and 40 kDa, and any integer value between 25 kDa and 35 kDa. The poly(ethylene glycol) molecule can be a linear molecule having a molecular weight of 30 kDa. The poly(ethylene glycol) molecule can have an aminooxy group capable of reacting with an acetyl group on a synthetic amino acid. The poly(ethylene glycol) molecule can be a 30 kDa aminooxy activated linear PEG capable of forming an oxime bond with the acetyl side chain of para-acetylphenylalanine.

One pIFN-α has a linear PEG that is about 30 kDa attached to the pAF residue.

The variants discussed above and further below can be further mixed into a formulation with various excipients, stabilizers, buffers, and other components for administration to animals. Identifying suitable formulations for stability, animal administration, and activity are not simple matters. Instead, the formulation must be tailored to each compound, the needs for purifying that compound, the stabilizer needed to maintain the compound, and various other formulation components.

Suitable salts for inclusion into the formulation include sodium chloride, potassium chloride or calcium chloride.

Sodium acetate can be used as a buffering agent and/or a stabilizing agent.

Suitable buffers can include phosphate-citrate buffer, phosphate buffer, citrate buffer, L-histidine, L-arginine hydrochloride, bicarbonate buffer, succinate buffer, citrate buffer, and TRIS buffer, either alone or in combination.

The formulation can also include a cryoprotectant. Cryoprotectants can include a cryoprotectant selected from the group consisting of hydroxypropyl-β-cyclodextrin (HPBCD), sucralose, and polyvinylpyrrolidone 4000 (PVP 4000).

The formulation may optionally include a surfactant. Suitable surfactants include polysorbates (e.g., polysorbate 80), dodecyl sulfate (SDS), lecithin either alone or in combination.

The formulation can be an aqueous composition or in the form of a reconstituted liquid composition or as a powder. The formulation can further stored in a vial or cartridge or in a pre-filled sterile syringe for ready administration to a subject.

The pH of the formulation can range from 4.0 to 7.0 or 4.5 to 6.5 when the formulation is in a liquid form.

Suitable viral infections that can be treated include without limitation a coronavirus, a pestivirus (swine fever virus or classical swine fever, CSF), transmissible gastroenteritis coronavirus (TGEV), swine arterivirus (PoAV), a porcine reproductive and respiratory syndrome virus (PRRSV), a porcine circovirus (PCV), a porcine epidemic diarrhea virus (PEDV), foot and mouth disease virus (FMDV), porcine coronavirus such as porcine deltacoronavirus (PDCoV), and swine influenza virus (SIV).

The administration of the variant or a formulation containing the variant can be a single dose or single dose followed by a secondary dosage 7 to 21 days after the first dose, e.g. about 14 days after the first dose. The animal is administered the variant in an amount of variant of about 25 μg/kg to about 150 μg/kg of variant per kg animal weight. Another effective range amount of the pIFN-α variant is about 50 μg/kg to about 100 μg/kg animal weight. The variant can be administered in a formulation or by itself. The variant can be administered once for example prior to an outbreak. The variant can also be administered after a virus outbreak to the herd to prevent further herd loss. The variant or a formulation thereof can be administered a second time. The second administration can be administered about 7 to about 21 days after the first administration, for example 14 days after the first administration. Further administrations may be contemplated if needed to reduce or prevent disease associated with viral infections.

It will be apparent to those skilled in the art that various modifications and variation can be made without departing from the spirit or scope of the compositions, compounds, and methods disclosed herein. Thus, it is intended that the present invention cover the modifications and variations of this invention provided they come within the scope of the appended claims and their equivalents.

EXAMPLES

Example 1: pAF Variants

Eleven (11) pAF variants are created and compared against the wild-type pIFN-α (wt). Of these, three pIFN-α variants are dropped from continued testing because of poor protein expression/production issues for the synthetic amino acids substituted at various points in the pIFN-α.

AXID2820 has plasmid pKG0083 with pIFN-α-E107amber and the proline-serine N-terminal insertion (FIG. 1). Numbering of the residues has been standardized to correspond to the wild type pIFN-α sequence (SEQ ID NO:4). The amino acid sequence of wild-type porcine interferon α-1 is obtained from GenBank (Accession Number X57191). The corresponding nucleic acid sequence is synthesized and cloned into an expression vector. The amber stop codon (TAG) is inserted at the glutamic acid codon corresponding to the amino acid position 107 (or other positions as indicated) of the mature wild-type coding region. The nucleic acids encoding Pro-Ser are inserted at the amino terminus after the initiating Methionine codon (AUG). To confirm that the cloning and subsequent mutagenesis had proceeded as expected with no introduction of unwanted mutation(s) the entire plasmid DNA sequence of pKG0083 is sequenced.

The eight (8) pIFN-α variants in Table 1 were capable of protein expression. These eight variants are also pegylated with a 30 kD aminooxy activated linear PEG. Pegylation of the variants is accomplished by adjusting the protein solution (at a protein concentration of approximately 20 mg/mL or greater) to pH 4.0 with 10% glacial acetic acid. Acetic hydrazide is added to a final concentration of 100 mM and oxyamino PEG is added in a molar ratio of between 1:1 and 2:1, or up to about 8:1, relative to the pIFN-α variant. The reaction is allowed to proceed for 1-3 days at 28-30° C. in the dark. The reaction is quenched by diluting the reaction 5-fold with 30 mM sodium acetate, pH 5.0. These 8 pegylated variants are analyzed using size exclusion chromatography (SEC), as shown in Table 1. The pIFN-α variants are the same as the wild-type pIFN-α except for a pAF substitution at the indicated residue, e.g., His7 was substituted with pAF, Arg34 was substituted with pAF and so forth. Protein concentration is indicated at mg/mL. "RP" stands as Reverse Phase (i.e. reverse phase chromatography, or RP-HPLC).

TABLE 1

Production of pegylated pIFNα variants.

| Sample | Protein Conc. (mg/mL) | % Main Peak by RP | % Monomer by SEC |
|---|---|---|---|
| pIFN-α wt SEQ ID NO: 4 | 1.5 | 69.4 | 99.5 |
| pIFNα-H7-PEG30 SEQ ID NO: 21 | 2.6 | 67.0 | 94.7 |
| pIFNα-R34-PEG30 SEQ ID NO: 22 | 2.2 | 73.8 | 99.6 |
| pIFNα-Q102-PEG30 SEQ ID NO: 6 | 1.9 | 68.1 | 97.7 |
| pIFNα-E103-PEG30 SEQ ID NO: 9 | 2.1 | 58.2 | 96.3 |
| pIFNα-E107-PEG30 SEQ ID NO: 12 | 1.9 | 60.2 | 98.2 |
| pIFNα-L112-PEG30 SEQ ID NO: 15 | 3.4 | 60.1 | 98.3 |
| pIFNα-Y136-PEG30 SEQ ID NO: 18 | 2.1 | 51.9 | 99.1 |
| pIFNα-H40-PEG30 SEQ ID NO: 23 | 1.9 | 52.1 | 98.7 |

SEC is accomplished using an HPLC system capable of multiple wavelength detection (Agilent 1100 or 1200, or equivalent). The mobile phase is 200 mM potassium phosphate, 250 mM potassium chloride, pH 6.0, 10% isopropanol (IPA).

These 8 variants are tested in an in vitro bioactivity assay. The commercially available interferon assay kit iLite™ huIFNα kit by Pestka Biomedical Laboratories, Inc. (Piscataway, N.J., USA) is used to test the biological activity of pIFN-α. The fold loss in activity of the PEG-variants is calculated relative to Ambrx WT protein as follows:

$$PEG-\text{Variant Fold loss} = \frac{EC50\ PEG-\text{variant}}{EC50\ Ambrx\ WT}$$

As shown in Table 2, of the eight tested, three of the pIFN-α variants had substantially less activity than wild-type unpegylated pIFN-α:

TABLE 2

| Rank Order | Test Sample | Fold loss in activity relative to WT pIFNα | EC50 [ng/mL] Test Sample | EC50 [ng/mL] Ambrx WT pIFNα |
|---|---|---|---|---|
| 1 | pIFNα E103-PEG30K | 8x | 184 | 22 |
| 2 | pIFNα L112-PEG30K | 15x | 475 | 32 |
| 3 | pIFNαα E107-PEG30K | 23x | 731 | 32 |
| 4 | pIFNαα Y136-PEG30K | 26x | 874 | 33 |
| 5 | pIFNαα Q102-PEG30K | 32x | 693 | 22 |
| 6 | pIFNαα H40-PEG30K | 171x | 5662 | 33 |
| 7 | pIFNαα H7-PEG30K | 387x | 8761 | 23 |
| no activity | pIFNαα R34-PEG30K | no activity | no activity | 23 |

The wild-type pIFN-α control lacks the signal peptide, has no inserted N-terminal amino acids (Methionine, Proline or Serine), has no pAF substitution for any amino acid, and is not pegylated (SEQ ID NO: 4).

As a result of these experiments, the pegylated pIFN-α variants having a pAF substitution at H40 (SEQ ID NO: 23), H7 (SEQ ID NO: 21), and R34 (SEQ ID NO: 22) are deemed not useful pIFN-α variants for treating viral infection in porcines given their low activity levels as compared to the wild type in the iLite™ huIFNα assay.

RP-HPLC analysis of both the pegylated and unpegylated variants for the results in Table 2 use a mobile phase A (0.05% TFA/water) and a mobile phase B (0.05% TFA/ACN).

Example 2: In Vivo Testing

Eighteen Sprague Dawley rats (n=3 group) are dosed at 0.2 mg/kg of each of 6 test samples (resuspended in 20 mM sodium acetate, pH 5.0, 100 mM NaCl, and 5% glycerol) subcutaneously in the scruff of their necks, distal to the catheter: (1) pIFNα-E103-PEG30K (pegylated SEQ ID NO: 9) (2) pIFNα-L112-PEG30K (pegylated SEQ ID NO: 15), (3) pIFNα-E107-PEG30K (pegylated SEQ ID NO: 12), (4) pIFNα-Y136-PEG30K (pegylated SEQ ID NO: 18), and (5) pIFNα-a-Q102-PEG30K (pegylated SEQ ID NO: 6).

The pIFN-α variants are solubilized in 20 mM sodium acetate at pH 5.0, 100 mM NaCl and 5% glycerol. Each animal is injected subcutaneously (i.e., intranuchally) with either one of the 5 variants or the wild type pIFN-α (the same as that used in Example 1) thus forming the 6 test groups of 3 rats each.

The sampling time points are: pre-dose and post dose at 1 hr, 6 hr, 24 hr, 48 hr, 72 hr, 144 hr, 192 hr, and 240 hours post dosing. Samples of blood are obtained via the jugular vein catheter or lateral tail vein or at the termination of the experiment via cardiac puncture and are processed by allowing the blood to clot and removing the resulting serum. The concentrations of each pegylated pIFN-α variant are determined using a ligand binding assay using an anti-PEG monoclonal capture antibody and a goat anti-porcine IFN-α polyclonal detection antibody. $AUC_{last}$, $C_{max}$, $T_{max}$ are calculated by analysis of the raw data using WINNONLIN® PK modeling software (Pharsight Corporation, now Certara USA, Inc.). The exposure ($AUC_{last}$) of the pegylated variants was divided by the exposure of the wild type pIFN (WT pIFN) to obtain fold differences. The results for the pegylated variants are as follows in Table 3:

TABLE 3

Bioavailability of pegylated IFN-α variants.

| Compound | Animal # | $AUC_{last}$ (ng*h/mL) | Fold difference vs. WT pIFN | $C_{max}$ (ng/mL) | $T_{max}$ h | Est. $T_{1/2}$ h |
|---|---|---|---|---|---|---|
| PEG Q102 | Mean | 12500 | 133 | 339 | 24 | 16.3 |
| pIFNα | SD | 686 | | 14.4 | 0 | 2.10 |
| PEG E107 | Mean | 9420 | 100 | 246 | 24 | 17.6 |
| pIFNα | SD | 2590 | | 77.6 | 0 | 3.93 |
| PEG L112 | Mean | 6000 | 64 | 165 | 24 | 12.7 |
| pIFNα | SD | 510 | | 15.6 | 0 | 1.11 |
| PEG E103 | Mean | 5210 | 55 | 147 | 18 | 11.7 |
| pIFNα | SD | 365 | | 12.5 | 10.4 | 0.479 |
| PEG Y136 | Mean | 5140 | 55 | 141 | 24 | 12.4 |
| pIFNα | SD | 788 | | 23.2 | 0 | 0.987 |
| WT pIFNα SEQ ID NO: 4 | Mean SD | 94.2 49.3 | 1 | 81 49.9 | 1 0 | NC NC |

"DN" stands for "dose normalized"; units for DN $AUC_{last}$ is (ng*h/mL)/(mg/kg) and for DN $C_{max}$ is (ng/mL)/(mg/kg). $C_{max}$ is used for half-life calculation. Nevertheless, the E107 pegylated pIFN-α variant has the highest half-life of the five (5) variants. "NC" means "not calculable" because the concentrations were measurable at only at two time-points.

As evidenced, exposure (in terms of $AUC_{last}$) is highest for PEG30K-Q102 and PEG30K-E107, and as presented in the table in decreasing order of exposure. All of the five tested pIFN-α variants have a higher exposure for pIFN-α than the wild type pIFN-α form (SEQ ID NO: 4). $T_{max}$ is generally observed at 24 hrs post-dose for pegylated pIFN-α variants as compared to 1 hour post-dose for wild type pIFN-α. For this experiment, $C_{max}$ is included in the half-life calculation due to insufficient data points in the terminal phase. As time at $C_{max}$ does not represent the true elimination phase, half-life estimates should be considered as an approximation.

It should be noted that the species heterology has no impact in this type of study.

Example 3: Characterization of Product Related Contaminants for pIFNα-E107pAF Based on mass spectroscopy (MS) of pIFN-αA-E107 (SEQ ID NO: 12), there are acetylated forms, a 58 Da form and oxidation contaminants. The variant becomes acetylated during biosynthesis inside the E. coli production strain. Thus, one option for pIFN-αA-E107 production is to add acetyltransferases at the appropriate production time or to use knockout ribosomal-protein-alanine acetyltransferase (RimJ) (N-terminal acetyltransferase). Additionally, small and large scale chromatography can be used for purification. Alternatively and as shown herein, the N-terminus sequence can be further modified to prevent acetylation from occurring on the variant altogether.

For chromatography means, one method is to use CAPTO Adhere Impres (GE Healthcare Lifesciences), which is a strong anion exchange multimodal BIOPROCESS chromatography medium (resin). This method is used with a mobile phase of 25 mM ammonium acetate (at pH 6.5), loading the unmodified (i.e. not pegylated) pIFN-α variant to a concentration of 1-5 mg/mL resin. The column is washed with 5 column volumes (CV) 25 mM ammonium acetate at pH 6.5.

Elution of the pIFN-αA variant is with a linear gradient to 100% elution buffer (5 mM acetic acid), and 0-100% B over 40 CV, whereby the oxidized pIFN-α peaks are removed. Peak One has an N-terminal pIFN-α without cysteine acetylation, whereas Peak 2 contained an acetylated form (+42 Da), a +58 Da form, a +58+1 Ox form (likely an acetylated and singly oxidized species), and a +58 Da+2 Ox form (likely an acetylated form with at least two oxidations).

Because of these results, a proline was inserted at the amino terminus of pIFN-α to prevent the acetylated forms. Thus a Pro-pIFNα-E107pAF (SEQ ID NO: SEQ ID NO: 13) was created. For clarity, numbering of amino acid positions always begins with the N-terminal cysteine (C1). The added proline becomes residue −1, and the N-terminal methionine (if any) becomes residue −2. A Pro-Ser insertion can also be made, wherein the peptide contains serine at the −1 position, proline at the −2 position, and possibly a methionine at the −3 position relative to the N-terminal cysteine. The addition of the proline removed the other peaks seen for the prior variant when analyzed via mass spectroscopy.

In Table 4 below, the Pro-pIFNα-E107pAF has a proline at the N terminus and a pAF substitution on E107. The activity of the Pro-pIFNα-E107pAF variant is compared to the activity of the variant lacking the addition of proline at the N-terminus, pIFNα-E107pAF. The variant having the added proline has fewer acetylated and oxidized variants. Note these variants are not pegylated and they do not include the signal sequence methionine.

TABLE 4

|  | Pro-pIFNα-E107pAF EC50, ng/mL | pIFNα-E107pAF EC50, ng/mL |
|---|---|---|
| Run 1 | 6.46 | 8.08 |
| Run 2 | 4.55 | 7.01 |

Example 4: Other N-Terminal Variants

Given the success with the proline addition to the N-terminus of pIFNα-E107pAF, other N-terminal variants were also assessed including a Serine (Ser, S) addition, a Pro-Ser (PS) addition, a His (H) addition, and a Ser-Gly (SG) addition to pIFNα-E107pAF. These N-terminal variants are not pegylated. The activity of these N-terminal variants (all are E107-pAF variants) was then assessed in the in vitro bioassay using iLite™ huIFNα kit by Pestka Biomedical Laboratories described above and the results are presented in Table 5.

TABLE 5

| Mutation | EC50 (ng/mL) |
|---|---|
| Pro-pINFα SEQ ID NO: 13 | 18.3 |
| S (−1) pINFα SEQ ID NO: 24 | 34.2 |
| SG (−2/−1) pINFα SEQ ID NO: 25 | 69.1 |
| PS (−2/−1) pINFα SEQ ID NO: 14 | 28.7 |
| H (−1) pINFα SEQ ID NO: 26 | 25.4 |

Pro-pINFα is the variant having the proline added at the amino terminus between the methionine (in the immature peptide) and the cysteine.

Example 5: Conjugation of the pIFN-α Variant with PEG

The pIFN-α-PS-E107 variant (SEQ ID NO: 14) is taken from the Capto chromatography pool after using Capto chromatography as per manufacturer instructions and 0.2 M glycine is added to the purified form. The pH of the mixture is adjusted to 4.0 with acetic acid. The pIFN-a variant is then concentrated to 8.2 mg/mL using an Amicon Ultra centrifugal filter according to manufacturer's instructions. Once concentrated, 30K linear PEG (PEG can be purchased commercially from NOF America Corporation or EMD Merck for examples) is added in a 8:1 molar ratio of pEG:pIFN-α variant. The PEG/pIFN-α variant mixture is then incubated at 28° C. for about 18 hours. This method results in >95% of the pIFN-α variant being conjugated with PEG after 18 hours of incubation.

The pegylated variant (pIFN-α-PS-E107-PEG30K) can then be purified as follows. A 143 mL SP650S Tosoh column can be used to purify the pegylated variant using a mobile phase of:
  A: 30 mM sodium acetate, pH 5.0
  B: 30 mM sodium acetate, 5% ethylene glycol, pH 5.0
  0 to 100% B over 20 column volumes.

Example 6: Comparison Testing of Different N-Terminal Variants

Activity assays are run for several variants in both their pegylated (30 KDa linear PEG) and unpegylated forms to assess the impact of pegylation on the variants having pAF substituted at E107 and having proline-serine at the amino terminus (SEQ ID NO: 14). The results are provided below in Table 6. Protein concentration, SEC, RP, and EC50 values are determined as discussed above. The pIFNα-P-E107-pAF is used as a comparator sample to reflect the results for protein without an amino terminal extension.

TABLE 6

| Sample | Protein Conc. (mg/mL) | SEC % Monomer | RP % Main Peak | EC50 (ng/mL) |
|---|---|---|---|---|
| pIFNα-PS-E107-pAF | 8.2 | 99.8 | 84.8 | 5.96 |
| pIFNα-PS-E107-30KPEG | 7.3 | 99.0 | 98.2 | 409.7 |
| pIFNα-P-E107-pAF |  |  |  | 4.27 |
| pIFNα-P-E107-30KPEG | 3.3 | 99.3 | 99.7 | 641.2 |

While testing the characterization of the variants, norleucine was observed to be misincorporated. Norleucine is known to be misincorporated at the amino acid methionine in high density fermentation with E. coli. This was observed in the fermentation runs performed. Norleucine incorporation was reduced by using one or more of the following steps: feeding the solutions with methionine, fermenting with complex media versus defined media (the complex media has one or more non-defined components in it including but limited to glycerol, salts, amino acids, vitamins, yeast extracts, plant and animal hydrolosates, peptones, and tryptones), and/or lowering the temperature of the reaction mixture post induction. L-methionine is added to the batch medium at a concentration of 1.2 mM as well as fed continuously via the feed solution which contains 20 mM L-methionine.

The pIFN-α variants are under the control of a T7 promoter. Addition of arabinose (the inducer) to the fermentation results in a cascade which enables production of the variants. Thus, post-induction means after the inducer, in this case arabinose, is added.

Example 7: Effect of Freeze Thawing on Pegylated and Unpegylated Variants

Samples were frozen and thawed over five cycles by freezing at 0° C. in 1.5 mL tubes and thawing in a room temperature water bath. No significant impact was observed for the high molecular weight (HMW) protein profile over the five cycles of freeze-thawing as evidenced below in Table 7:

TABLE 7

| Freeze/Thaw Cycle | pIFNα-PS-E107pAF | | pIFNα-PS-E107-30KPEG | |
|---|---|---|---|---|
| | % Main Peak | % HMW | % Main Peak | % HMW |
| 0 | 99.8 | 0.2 | 99.0 | 0.7 |
| 1 | 99.8 | 0.2 | 99.0 | 0.8 |
| 3 | 99.8 | 0.2 | 99.0 | 0.9 |
| 5 | 99.8 | 0.2 | 99.0 | 0.9 |

Table 7 reflects the differences between the pegylated and unpegylated variants having the proline-serine at the N-terminus as well as the pAF substituted at E107, wherein the variant has the proline-serine insertion at the amino terminus (pIFNα-PS-E107-30), i.e. at residues −2 and −1.

SEQUENCE LISTING

```
<160> NUMBER OF SEQ ID NOS: 26

<210> SEQ ID NO 1
<211> LENGTH: 168
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xa is Pro or absent
<220> FEATURE:
<221> NAME/KEY: misc_feature
<222> LOCATION: (2)..(2)
<223> OTHER INFORMATION: Xb is Pro, Ser or absent, wherein when Xb is
      absent, Xa is absent, when Xb is Pro, Xa is absent, and when Xb is
      Ser, Xa is Pro
<220> FEATURE:
<221> NAME/KEY: misc_feature
<222> LOCATION: (104)..(104)
<223> OTHER INFORMATION: may be substituted with a synthetic amino acid
<220> FEATURE:
<221> NAME/KEY: MISC_FEATURE
<222> LOCATION: (105)..(105)
<223> OTHER INFORMATION: may be substituted with a synthetic amino acid
<220> FEATURE:
<221> NAME/KEY: MISC_FEATURE
<222> LOCATION: (109)..(109)
<223> OTHER INFORMATION: may be substituted with a synthetic amino acid
<220> FEATURE:
<221> NAME/KEY: MISC_FEATURE
<222> LOCATION: (114)..(114)
<223> OTHER INFORMATION: may be substituted with a synthetic amino acid
<220> FEATURE:
<221> NAME/KEY: MISC_FEATURE
<222> LOCATION: (138)..(138)
<223> OTHER INFORMATION: may be substituted with a synthetic amino acid

<400> SEQUENCE: 1

Xaa Xaa Cys Asp Leu Pro Gln Thr His Ser Leu Ala His Thr Arg Ala
1               5                   10                  15

Leu Arg Leu Leu Ala Gln Met Arg Arg Ile Ser Pro Phe Ser Cys Leu
            20                  25                  30

Asp His Arg Arg Asp Phe Gly Ser Pro His Glu Ala Phe Gly Gly Asn
        35                  40                  45

Gln Val Gln Lys Ala Gln Ala Met Ala Leu Val His Glu Met Leu Gln
    50                  55                  60

Gln Thr Phe Gln Leu Phe Ser Thr Glu Gly Ser Ala Ala Ala Trp Asn
```

```
                65                  70                  75                  80
Glu Ser Leu Leu His Gln Phe Tyr Thr Gly Leu Asp Gln Gln Leu Arg
                    85                  90                  95

Asp Leu Glu Ala Cys Val Met Gln Glu Ala Gly Leu Glu Gly Thr Pro
                100                 105                 110

Leu Leu Glu Glu Asp Ser Ile Arg Ala Val Arg Lys Tyr Phe His Arg
            115                 120                 125

Leu Thr Leu Tyr Leu Gln Glu Lys Ser Tyr Ser Pro Cys Ala Trp Glu
        130                 135                 140

Ile Val Arg Ala Glu Val Met Arg Ser Phe Ser Ser Ser Arg Asn Leu
145                 150                 155                 160

Gln Asp Arg Leu Arg Lys Lys Glu
                165

<210> SEQ ID NO 2
<211> LENGTH: 169
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: may be removed in mature polypeptide
<220> FEATURE:
<221> NAME/KEY: MISC_FEATURE
<222> LOCATION: (2)..(2)
<223> OTHER INFORMATION: Xa is Pro or absent
<220> FEATURE:
<221> NAME/KEY: MISC_FEATURE
<222> LOCATION: (3)..(3)
<223> OTHER INFORMATION: Xb is Pro, Ser or absent, wherein when Xb is
      absent, Xa is absent, when Xb is Pro, Xa is absent, and when Xb is
      Ser, Xa is Pro
<220> FEATURE:
<221> NAME/KEY: MISC_FEATURE
<222> LOCATION: (105)..(105)
<223> OTHER INFORMATION: may be substituted with a synthetic amino acid
<220> FEATURE:
<221> NAME/KEY: MISC_FEATURE
<222> LOCATION: (106)..(106)
<223> OTHER INFORMATION: may be substituted with a synthetic amino acid
<220> FEATURE:
<221> NAME/KEY: MISC_FEATURE
<222> LOCATION: (110)..(110)
<223> OTHER INFORMATION: may be substituted with a synthetic amino acid
<220> FEATURE:
<221> NAME/KEY: MISC_FEATURE
<222> LOCATION: (115)..(115)
<223> OTHER INFORMATION: may be substituted with a synthetic amino acid
<220> FEATURE:
<221> NAME/KEY: MISC_FEATURE
<222> LOCATION: (139)..(139)
<223> OTHER INFORMATION: may be substituted with a synthetic amino acid

<400> SEQUENCE: 2

Met Xaa Xaa Cys Asp Leu Pro Gln Thr His Ser Leu Ala His Thr Arg
1               5                   10                  15

Ala Leu Arg Leu Leu Ala Gln Met Arg Arg Ile Ser Pro Phe Ser Cys
                20                  25                  30

Leu Asp His Arg Arg Asp Phe Gly Ser Pro His Glu Ala Phe Gly Gly
            35                  40                  45

Asn Gln Val Gln Lys Ala Gln Ala Met Ala Leu Val His Glu Met Leu
        50                  55                  60

Gln Gln Thr Phe Gln Leu Phe Ser Thr Glu Gly Ser Ala Ala Ala Trp
65                  70                  75                  80
```

-continued

```
Asn Glu Ser Leu Leu His Gln Phe Tyr Thr Gly Leu Asp Gln Gln Leu
                 85                  90                  95
Arg Asp Leu Glu Ala Cys Val Met Gln Glu Ala Gly Leu Glu Gly Thr
            100                 105                 110
Pro Leu Leu Glu Glu Asp Ser Ile Arg Ala Val Arg Lys Tyr Phe His
        115                 120                 125
Arg Leu Thr Leu Tyr Leu Gln Glu Lys Ser Tyr Ser Pro Cys Ala Trp
130                 135                 140
Glu Ile Val Arg Ala Glu Val Met Arg Ser Phe Ser Ser Ser Arg Asn
145                 150                 155                 160
Leu Gln Asp Arg Leu Arg Lys Lys Glu
                165
```

<210> SEQ ID NO 3
<211> LENGTH: 189
<212> TYPE: PRT
<213> ORGANISM: Sus scrofa
<220> FEATURE:
<221> NAME/KEY: mat_peptide
<222> LOCATION: (24)..(189)

<400> SEQUENCE: 3

```
Met Ala Pro Thr Ser Ala Phe Leu Thr Ala Leu Val Leu Leu Ser Cys
            -20                 -15                 -10
Asn Ala Ile Cys Ser Leu Gly Cys Asp Leu Pro Gln Thr His Ser Leu
         -5                  -1   1               5
Ala His Thr Arg Ala Leu Arg Leu Leu Ala Gln Met Arg Arg Ile Ser
 10                  15                  20                  25
Pro Phe Ser Cys Leu Asp His Arg Arg Asp Phe Gly Ser Pro His Glu
                 30                  35                  40
Ala Phe Gly Gly Asn Gln Val Gln Lys Ala Gln Ala Met Ala Leu Val
             45                  50                  55
His Glu Met Leu Gln Gln Thr Phe Gln Leu Phe Ser Thr Glu Gly Ser
         60                  65                  70
Ala Ala Ala Trp Asn Glu Ser Leu Leu His Gln Phe Tyr Thr Gly Leu
 75                  80                  85
Asp Gln Gln Leu Arg Asp Leu Glu Ala Cys Val Met Gln Glu Ala Gly
 90                  95                 100                 105
Leu Glu Gly Thr Pro Leu Leu Glu Glu Asp Ser Ile Arg Ala Val Arg
                110                 115                 120
Lys Tyr Phe His Arg Leu Thr Leu Tyr Leu Gln Glu Lys Ser Tyr Ser
             125                 130                 135
Pro Cys Ala Trp Glu Ile Val Arg Ala Glu Val Met Arg Ser Phe Ser
         140                 145                 150
Ser Ser Arg Asn Leu Gln Asp Arg Leu Arg Lys Lys Glu
     155                 160                 165
```

<210> SEQ ID NO 4
<211> LENGTH: 166
<212> TYPE: PRT
<213> ORGANISM: Sus scrofa
<220> FEATURE:
<221> NAME/KEY: MISC_FEATURE
<222> LOCATION: (102)..(102)
<223> OTHER INFORMATION: may be substituted with a synthetic amino acid
<220> FEATURE:
<221> NAME/KEY: MISC_FEATURE
<222> LOCATION: (103)..(103)
<223> OTHER INFORMATION: may be substituted with a synthetic amino acid
<220> FEATURE:

<221> NAME/KEY: MISC_FEATURE
<222> LOCATION: (107)..(107)
<223> OTHER INFORMATION: may be substituted with a synthetic amino acid
<220> FEATURE:
<221> NAME/KEY: MISC_FEATURE
<222> LOCATION: (112)..(112)
<223> OTHER INFORMATION: may be substituted with a synthetic amino acid
<220> FEATURE:
<221> NAME/KEY: MISC_FEATURE
<222> LOCATION: (136)..(136)
<223> OTHER INFORMATION: may be substituted with a synthetic amino acid

<400> SEQUENCE: 4

```
Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
            20                  25                  30

Arg Arg Asp Phe Gly Ser Pro His Glu Ala Phe Gly Gly Asn Gln Val
        35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Gln Glu Ala Gly Leu Glu Gly Thr Pro Leu Leu
            100                 105                 110

Glu Glu Asp Ser Ile Arg Ala Val Arg Lys Tyr Phe His Arg Leu Thr
        115                 120                 125

Leu Tyr Leu Gln Glu Lys Ser Tyr Ser Pro Cys Ala Trp Glu Ile Val
130                 135                 140

Arg Ala Glu Val Met Arg Ser Phe Ser Ser Ser Arg Asn Leu Gln Asp
145                 150                 155                 160

Arg Leu Arg Lys Lys Glu
                165
```

<210> SEQ ID NO 5
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: may be removed in mature polypeptide
<220> FEATURE:
<221> NAME/KEY: MISC_FEATURE
<222> LOCATION: (103)..(103)
<223> OTHER INFORMATION: may be substituted with a synthetic amino acid
<220> FEATURE:
<221> NAME/KEY: MISC_FEATURE
<222> LOCATION: (104)..(104)
<223> OTHER INFORMATION: may be substituted with a synthetic amino acid
<220> FEATURE:
<221> NAME/KEY: MISC_FEATURE
<222> LOCATION: (108)..(108)
<223> OTHER INFORMATION: may be substituted with a synthetic amino acid
<220> FEATURE:
<221> NAME/KEY: MISC_FEATURE
<222> LOCATION: (113)..(113)
<223> OTHER INFORMATION: may be substituted with a synthetic amino acid
<220> FEATURE:
<221> NAME/KEY: MISC_FEATURE
<222> LOCATION: (137)..(137)
<223> OTHER INFORMATION: may be substituted with a synthetic amino acid

<400> SEQUENCE: 5

Met Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
                20                  25                  30

His Arg Arg Asp Phe Gly Ser Pro His Glu Ala Phe Gly Gly Asn Gln
            35                  40                  45

Val Gln Lys Ala Gln Ala Met Ala Leu Val His Glu Met Leu Gln Gln
    50                  55                  60

Thr Phe Gln Leu Phe Ser Thr Glu Gly Ser Ala Ala Trp Asn Glu
65                  70                  75                  80

Ser Leu Leu His Gln Phe Tyr Thr Gly Leu Asp Gln Gln Leu Arg Asp
                85                  90                  95

Leu Glu Ala Cys Val Met Gln Glu Ala Gly Leu Glu Gly Thr Pro Leu
                100                 105                 110

Leu Glu Glu Asp Ser Ile Arg Ala Val Arg Lys Tyr Phe His Arg Leu
                115                 120                 125

Thr Leu Tyr Leu Gln Glu Lys Ser Tyr Ser Pro Cys Ala Trp Glu Ile
    130                 135                 140

Val Arg Ala Glu Val Met Arg Ser Phe Ser Ser Ser Arg Asn Leu Gln
145                 150                 155                 160

Asp Arg Leu Arg Lys Lys Glu
                165

<210> SEQ ID NO 6
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (102)..(102)
<223> OTHER INFORMATION: para-acetyl-phenylalanine (pAF)

<400> SEQUENCE: 6

Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
                20                  25                  30

Arg Arg Asp Phe Gly Ser Pro His Glu Ala Phe Gly Gly Asn Gln Val
            35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Xaa Glu Ala Gly Leu Glu Gly Thr Pro Leu Leu
                100                 105                 110

Glu Glu Asp Ser Ile Arg Ala Val Arg Lys Tyr Phe His Arg Leu Thr
                115                 120                 125

Leu Tyr Leu Gln Glu Lys Ser Tyr Ser Pro Cys Ala Trp Glu Ile Val
    130                 135                 140

Arg Ala Glu Val Met Arg Ser Phe Ser Ser Ser Arg Asn Leu Gln Asp
145                 150                 155                 160

Arg Leu Arg Lys Lys Glu
            165

<210> SEQ ID NO 7
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (103)..(103)
<223> OTHER INFORMATION: para-acetyl-phenylalanine (pAF)

<400> SEQUENCE: 7

Pro Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
            20                  25                  30

His Arg Arg Asp Phe Gly Ser Pro His Glu Ala Phe Gly Gly Asn Gln
        35                  40                  45

Val Gln Lys Ala Gln Ala Met Ala Leu Val His Glu Met Leu Gln Gln
    50                  55                  60

Thr Phe Gln Leu Phe Ser Thr Glu Gly Ser Ala Ala Trp Asn Glu
65                  70                  75                  80

Ser Leu Leu His Gln Phe Tyr Thr Gly Leu Asp Gln Gln Leu Arg Asp
                85                  90                  95

Leu Glu Ala Cys Val Met Xaa Glu Ala Gly Leu Glu Gly Thr Pro Leu
            100                 105                 110

Leu Glu Glu Asp Ser Ile Arg Ala Val Arg Lys Tyr Phe His Arg Leu
        115                 120                 125

Thr Leu Tyr Leu Gln Glu Lys Ser Tyr Ser Pro Cys Ala Trp Glu Ile
    130                 135                 140

Val Arg Ala Glu Val Met Arg Ser Phe Ser Ser Ser Arg Asn Leu Gln
145                 150                 155                 160

Asp Arg Leu Arg Lys Lys Glu
            165

<210> SEQ ID NO 8
<211> LENGTH: 168
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (104)..(104)
<223> OTHER INFORMATION: para-acetyl-phenylalanine (pAF)

<400> SEQUENCE: 8

Pro Ser Cys Asp Leu Pro Gln Thr His Ser Leu Ala His Thr Arg Ala
1               5                   10                  15

Leu Arg Leu Leu Ala Gln Met Arg Arg Ile Ser Pro Phe Ser Cys Leu
            20                  25                  30

Asp His Arg Arg Asp Phe Gly Ser Pro His Glu Ala Phe Gly Gly Asn
        35                  40                  45

Gln Val Gln Lys Ala Gln Ala Met Ala Leu Val His Glu Met Leu Gln
    50                  55                  60

Gln Thr Phe Gln Leu Phe Ser Thr Glu Gly Ser Ala Ala Ala Trp Asn
65                  70                  75                  80

-continued

```
Glu Ser Leu Leu His Gln Phe Tyr Thr Gly Leu Asp Gln Gln Leu Arg
                85                  90                  95

Asp Leu Glu Ala Cys Val Met Xaa Glu Ala Gly Leu Glu Gly Thr Pro
            100                 105                 110

Leu Leu Glu Glu Asp Ser Ile Arg Ala Val Arg Lys Tyr Phe His Arg
        115                 120                 125

Leu Thr Leu Tyr Leu Gln Glu Lys Ser Tyr Ser Pro Cys Ala Trp Glu
    130                 135                 140

Ile Val Arg Ala Glu Val Met Arg Ser Phe Ser Ser Arg Asn Leu
145                 150                 155                 160

Gln Asp Arg Leu Arg Lys Lys Glu
                165

<210> SEQ ID NO 9
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (103)..(103)
<223> OTHER INFORMATION: para-acetyl-phenylalanine (pAF)

<400> SEQUENCE: 9

Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
            20                  25                  30

Arg Arg Asp Phe Gly Ser Pro His Glu Ala Phe Gly Gly Asn Gln Val
        35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Gln Xaa Ala Gly Leu Glu Gly Thr Pro Leu Leu
            100                 105                 110

Glu Glu Asp Ser Ile Arg Ala Val Arg Lys Tyr Phe His Arg Leu Thr
        115                 120                 125

Leu Tyr Leu Gln Glu Lys Ser Tyr Ser Pro Cys Ala Trp Glu Ile Val
    130                 135                 140

Arg Ala Glu Val Met Arg Ser Phe Ser Ser Arg Asn Leu Gln Asp
145                 150                 155                 160

Arg Leu Arg Lys Lys Glu
                165

<210> SEQ ID NO 10
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (104)..(104)
<223> OTHER INFORMATION: para-acetyl-phenylalanine (pAF)

<400> SEQUENCE: 10
```

```
Pro Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
            20                  25                  30

His Arg Arg Asp Phe Gly Ser Pro His Glu Ala Phe Gly Gly Asn Gln
        35                  40                  45

Val Gln Lys Ala Gln Ala Met Ala Leu Val His Glu Met Leu Gln Gln
    50                  55                  60

Thr Phe Gln Leu Phe Ser Thr Glu Gly Ser Ala Ala Trp Asn Glu
65                  70                  75                  80

Ser Leu Leu His Gln Phe Tyr Thr Gly Leu Asp Gln Gln Leu Arg Asp
                85                  90                  95

Leu Glu Ala Cys Val Met Gln Xaa Ala Gly Leu Glu Gly Thr Pro Leu
            100                 105                 110

Leu Glu Glu Asp Ser Ile Arg Ala Val Arg Lys Tyr Phe His Arg Leu
            115                 120                 125

Thr Leu Tyr Leu Gln Glu Lys Ser Tyr Ser Pro Cys Ala Trp Glu Ile
    130                 135                 140

Val Arg Ala Glu Val Met Arg Ser Phe Ser Ser Ser Arg Asn Leu Gln
145                 150                 155                 160

Asp Arg Leu Arg Lys Lys Glu
                165
```

<210

<210> SEQ ID NO 12
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (107)..(107)
<223> OTHER INFORMATION: para-acetyl-phenylalanine (pAF)

<400> SEQUENCE: 12

Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
            20                  25                  30

Arg Arg Asp Phe Gly Ser Pro His Glu Ala Phe Gly Gly Asn Gln Val
        35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Gln Glu Ala Gly Leu Xaa Gly Thr Pro Leu Leu
            100                 105                 110

Glu Glu Asp Ser Ile Arg Ala Val Arg Lys Tyr Phe His Arg Leu Thr
        115                 120                 125

Leu Tyr Leu Gln Glu Lys Ser Tyr Ser Pro Cys Ala Trp Glu Ile Val
    130                 135                 140

Arg Ala Glu Val Met Arg Ser Phe Ser Ser Arg Asn Leu Gln Asp
145                 150                 155                 160

Arg Leu Arg Lys Lys Glu
                165

<210> SEQ ID NO 13
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (108)..(108)
<223> OTHER INFORMATION: para-acetyl-phenylalanine (pAF)

<400> SEQUENCE: 13

Pro Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
            20                  25                  30

His Arg Arg Asp Phe Gly Ser Pro His Glu Ala Phe Gly Gly Asn Gln
        35                  40                  45

Val Gln Lys Ala Gln Ala Met Ala Leu Val His Glu Met Leu Gln Gln
    50                  55                  60

Thr Phe Gln Leu Phe Ser Thr Glu Gly Ser Ala Ala Ala Trp Asn Glu
65                  70                  75                  80

Ser Leu Leu His Gln Phe Tyr Thr Gly Leu Asp Gln Gln Leu Arg Asp
                85                  90                  95

```
Leu Glu Ala Cys Val Met Gln Glu Ala Gly Leu Xaa Gly Thr Pro Leu
                100                 105                 110

Leu Glu Glu Asp Ser Ile Arg Ala Val Arg Lys Tyr Phe His Arg Leu
            115                 120                 125

Thr Leu Tyr Leu Gln Lys Ser Tyr Ser Pro Cys Ala Trp Glu Ile
130                 135                 140

Val Arg Ala Glu Val Met Arg Ser Phe Ser Ser Arg Asn Leu Gln
145                 150                 155                 160

Asp Arg Leu Arg Lys Lys Glu
                165

<210> SEQ ID NO 14
<211> LENGTH: 168
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (109)..(109)
<223> OTHER INFORMATION: para-acetyl-phenylalanine (pAF)

<400> SEQUENCE: 14

Pro Ser Cys Asp Leu Pro Gln Thr His Ser Leu Ala His Thr Arg Ala
1               5                   10                  15

Leu Arg Leu Leu Ala Gln Met Arg Arg Ile Ser Pro Phe Ser Cys Leu
                20                  25                  30

Asp His Arg Arg Asp Phe Gly Ser Pro His Glu Ala Phe Gly Gly Asn
            35                  40                  45

Gln Val Gln Lys Ala Gln Ala Met Ala Leu Val His Glu Met Leu Gln
    50                  55                  60

Gln Thr Phe Gln Leu Phe Ser Thr Glu Gly Ser Ala Ala Ala Trp Asn
65                  70                  75                  80

Glu Ser Leu Leu His Gln Phe Tyr Thr Gly Leu Asp Gln Gln Leu Arg
                85                  90                  95

Asp Leu Glu Ala Cys Val Met Gln Glu Ala Gly Leu Xaa Gly Thr Pro
                100                 105                 110

Leu Leu Glu Glu Asp Ser Ile Arg Ala Val Arg Lys Tyr Phe His Arg
            115                 120                 125

Leu Thr Leu Tyr Leu Gln Lys Ser Tyr Ser Pro Cys Ala Trp Glu
130                 135                 140

Ile Val Arg Ala Glu Val Met Arg Ser Phe Ser Ser Arg Asn Leu
145                 150                 155                 160

Gln Asp Arg Leu Arg Lys Lys Glu
                165

<210> SEQ ID NO 15
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (112)..(112)
<223> OTHER INFORMATION: para-acetyl-phenylalanine (pAF)

<400> SEQUENCE: 15

Cys Asp Leu Pro Gln Thr His Ser Leu Ala His Thr Arg Ala Leu Arg
1               5                   10                  15
```

Leu Leu Ala Gln Met Arg Arg Ile Ser Pro Phe Ser Cys Leu Asp His
        20                  25                  30

Arg Arg Asp Phe Gly Ser Pro His Glu Ala Phe Gly Gly Asn Gln Val
            35                  40                  45

Gln Lys Ala Gln Ala Met Ala Leu Val His Glu Met Leu Gln Gln Thr
 50                  55                  60

Phe Gln Leu Phe Ser Thr Glu Gly Ser Ala Ala Ala Trp Asn Glu Ser
 65                  70                  75                  80

Leu Leu His Gln Phe Tyr Thr Gly Leu Asp Gln Gln Leu Arg Asp Leu
                 85                  90                  95

Glu Ala Cys Val Met Gln Glu Ala Gly Leu Glu Gly Thr Pro Leu Xaa
                100                 105                 110

Glu Glu Asp Ser Ile Arg Ala Val Arg Lys Tyr Phe His Arg Leu Thr
            115                 120                 125

Leu Tyr Leu Gln Glu Lys Ser Tyr Ser Pro Cys Ala Trp Glu Ile Val
130                 135                 140

Arg Ala Glu Val Met Arg Ser Phe Ser Ser Ser Arg Asn Leu Gln Asp
145                 150                 155                 160

Arg Leu Arg Lys Lys Glu
                165

<210> SEQ ID NO 16
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (113)..(113)
<223> OTHER INFORMATION: para-acetyl-phenylalanine (pAF)

<400> SEQUENCE: 16

Pro Cys Asp Leu Pro Gln Thr His Ser Leu Ala His Thr Arg Ala Leu
 1               5                  10                  15

Arg Leu Leu Ala Gln Met Arg Arg Ile Ser Pro Phe Ser Cys Leu Asp
                 20                  25                  30

His Arg Arg Asp Phe Gly Ser Pro His Glu Ala Phe Gly Gly Asn Gln
             35                  40                  45

Val Gln Lys Ala Gln Ala Met Ala Leu Val His Glu Met Leu Gln Gln
 50                  55                  60

Thr Phe Gln Leu Phe Ser Thr Glu Gly Ser Ala Ala Ala Trp Asn Glu
 65                  70                  75                  80

Ser Leu Leu His Gln Phe Tyr Thr Gly Leu Asp Gln Gln Leu Arg Asp
                 85                  90                  95

Leu Glu Ala Cys Val Met Gln Glu Ala Gly Leu Glu Gly Thr Pro Leu
                100                 105                 110

Xaa Glu Glu Asp Ser Ile Arg Ala Val Arg Lys Tyr Phe His Arg Leu
        115                 120                 125

Thr Leu Tyr Leu Gln Glu Lys Ser Tyr Ser Pro Cys Ala Trp Glu Ile
130                 135                 140

Val Arg Ala Glu Val Met Arg Ser Phe Ser Ser Ser Arg Asn Leu Gln
145                 150                 155                 160

Asp Arg Leu Arg Lys Lys Glu
                165

-continued

```
<210> SEQ ID NO 17
<211> LENGTH: 168
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (114)..(114)
<223> OTHER INFORMATION: para-acetyl-phenylalanine (pAF)

<400> SEQUENCE: 17

Pro Ser Cys Asp Leu Pro Gln Thr His Ser Leu Ala His Thr Arg Ala
1               5                   10                  15

Leu Arg Leu Leu Ala Gln Met Arg Arg Ile Ser Pro Phe Ser Cys Leu
            20                  25                  30

Asp His Arg Arg Asp Phe Gly Ser Pro His Glu Ala Phe Gly Gly Asn
        35                  40                  45

Gln Val Gln Lys Ala Gln Ala Met Ala Leu Val His Glu Met Leu Gln
    50                  55                  60

Gln Thr Phe Gln Leu Phe Ser Thr Glu Gly Ser Ala Ala Ala Trp Asn
65                  70                  75                  80

Glu Ser Leu Leu His Gln Phe Tyr Thr Gly Leu Asp Gln Gln Leu Arg
                85                  90                  95

Asp Leu Glu Ala Cys Val Met Gln Glu Ala Gly Leu Glu Gly Thr Pro
            100                 105                 110

Leu Xaa Glu Glu Asp Ser Ile Arg Ala Val Arg Lys Tyr Phe His Arg
        115                 120                 125

Leu Thr Leu Tyr Leu Gln Glu Lys Ser Tyr Ser Pro Cys Ala Trp Glu
    130                 135                 140

Ile Val Arg Ala Glu Val Met Arg Ser Phe Ser Ser Ser Arg Asn Leu
145                 150                 155                 160

Gln Asp Arg Leu Arg Lys Lys Glu
                165

<210> SEQ ID NO 18
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (136)..(136)
<223> OTHER INFORMATION: para-acetyl-phenylalanine (pAF)

<400> SEQUENCE: 18

Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
            20                  25                  30

Arg Arg Asp Phe Gly Ser Pro His Glu Ala Phe Gly Gly Asn Gln Val
        35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Gln Glu Ala Gly Leu Glu Gly Thr Pro Leu Leu
```

```
                    100                 105                 110
Glu Glu Asp Ser Ile Arg Ala Val Arg Lys Tyr Phe His Arg Leu Thr
            115                 120                 125

Leu Tyr Leu Gln Glu Lys Ser Xaa Ser Pro Cys Ala Trp Glu Ile Val
    130                 135                 140

Arg Ala Glu Val Met Arg Ser Phe Ser Ser Ser Arg Asn Leu Gln Asp
145                 150                 155                 160

Arg Leu Arg Lys Lys Glu
                165

<210> SEQ ID NO 19
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (137)..(137)
<223> OTHER INFORMATION: para-acetyl-phenylalanine (pAF)

<400> SEQUENCE: 19

Pro Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
            20                  25                  30

His Arg Arg Asp Phe Gly Ser Pro His Glu Ala Phe Gly Gly Asn Gln
        35                  40                  45

Val Gln Lys Ala Gln Ala Met Ala Leu Val His Glu Met Leu Gln Gln
    50                  55                  60

Thr Phe Gln Leu Phe Ser Thr Glu Gly Ser Ala Ala Trp Asn Glu
65                  70                  75                  80

Ser Leu Leu His Gln Phe Tyr Thr Gly Leu Asp Gln Gln Leu Arg Asp
                85                  90                  95

Leu Glu Ala Cys Val Met Gln Glu Ala Gly Leu Glu Gly Thr Pro Leu
            100                 105                 110

Leu Glu Glu Asp Ser Ile Arg Ala Val Arg Lys Tyr Phe His Arg Leu
        115                 120                 125

Thr Leu Tyr Leu Gln Glu Lys Ser Xaa Ser Pro Cys Ala Trp Glu Ile
    130                 135                 140

Val Arg Ala Glu Val Met Arg Ser Phe Ser Ser Ser Arg Asn Leu Gln
145                 150                 155                 160

Asp Arg Leu Arg Lys Lys Glu
                165

<210> SEQ ID NO 20
<211> LENGTH: 168
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (138)..(138)
<223> OTHER INFORMATION: para-acetyl-phenylalanine (pAF)

<400> SEQUENCE: 20

Pro Ser Cys Asp Leu Pro Gln Thr His Ser Leu Ala His Thr Arg Ala
1               5                   10                  15

Leu Arg Leu Leu Ala Gln Met Arg Arg Ile Ser Pro Phe Ser Cys Leu
```

```
                    20                  25                  30
Asp His Arg Arg Asp Phe Gly Ser Pro His Glu Ala Phe Gly Gly Asn
                35                  40                  45
Gln Val Gln Lys Ala Gln Ala Met Ala Leu Val His Glu Met Leu Gln
         50                  55                  60
Gln Thr Phe Gln Leu Phe Ser Thr Glu Gly Ser Ala Ala Ala Trp Asn
 65                  70                  75                  80
Glu Ser Leu Leu His Gln Phe Tyr Thr Gly Leu Asp Gln Gln Leu Arg
                 85                  90                  95
Asp Leu Glu Ala Cys Val Met Gln Glu Ala Gly Leu Glu Gly Thr Pro
                100                 105                 110
Leu Leu Glu Glu Asp Ser Ile Arg Ala Val Arg Lys Tyr Phe His Arg
                115                 120                 125
Leu Thr Leu Tyr Leu Gln Glu Lys Ser Xaa Ser Pro Cys Ala Trp Glu
            130                 135                 140
Ile Val Arg Ala Glu Val Met Arg Ser Phe Ser Ser Ser Arg Asn Leu
145                 150                 155                 160
Gln Asp Arg Leu Arg Lys Lys Glu
                165

<210> SEQ ID NO 21
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: para-acetyl-phenylalanine (pAF)

<400> SEQUENCE: 21

Cys Asp Leu Pro Gln Thr Xaa Ser Leu Ala His Thr Arg Ala Leu Arg
 1               5                  10                  15
Leu Leu Ala Gln Met Arg Arg Ile Ser Pro Phe Ser Cys Leu Asp His
                20                  25                  30
Arg Arg Asp Phe Gly Ser Pro His Glu Ala Phe Gly Gly Asn Gln Val
            35                  40                  45
Gln Lys Ala Gln Ala Met Ala Leu Val His Glu Met Leu Gln Gln Thr
         50                  55                  60
Phe Gln Leu Phe Ser Thr Glu Gly Ser Ala Ala Ala Trp Asn Glu Ser
 65                  70                  75                  80
Leu Leu His Gln Phe Tyr Thr Gly Leu Asp Gln Gln Leu Arg Asp Leu
                 85                  90                  95
Glu Ala Cys Val Met Gln Glu Ala Gly Leu Glu Gly Thr Pro Leu Leu
                100                 105                 110
Glu Glu Asp Ser Ile Arg Ala Val Arg Lys Tyr Phe His Arg Leu Thr
            115                 120                 125
Leu Tyr Leu Gln Glu Lys Ser Tyr Ser Pro Cys Ala Trp Glu Ile Val
        130                 135                 140
Arg Ala Glu Val Met Arg Ser Phe Ser Ser Ser Arg Asn Leu Gln Asp
145                 150                 155                 160
Arg Leu Arg Lys Lys Glu
                165

<210> SEQ ID NO 22
<211> LENGTH: 166
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (34)..(34)
<223> OTHER INFORMATION: para-acetyl-phenylalanine (pAF)

<400> SEQUENCE: 22
```

Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
            20                  25                  30

Arg Xaa Asp Phe Gly Ser Pro His Glu Ala Phe Gly Gly Asn Gln Val
        35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Gln Glu Ala Gly Leu Glu Gly Thr Pro Leu Leu
            100                 105                 110

Glu Glu Asp Ser Ile Arg Ala Val Arg Lys Tyr Phe His Arg Leu Thr
            115                 120                 125

Leu Tyr Leu Gln Glu Lys Ser Tyr Ser Pro Cys Ala Trp Glu Ile Val
130                 135                 140

Arg Ala Glu Val Met Arg Ser Phe Ser Ser Arg Asn Leu Gln Asp
145                 150                 155                 160

Arg Leu Arg Lys Lys Glu
                165

```
<210> SEQ ID NO 23
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (40)..(40)
<223> OTHER INFORMATION: para-acetyl-phenylalanine (pAF)

<400> SEQUENCE: 23
```

Cys Asp Leu Pro Gln Thr His Ser Leu Ala His Thr Arg Ala Leu Arg
1               5                   10                  15

Leu Leu Ala Gln Met Arg Arg Ile Ser Pro Phe Ser Cys Leu Asp His
            20                  25                  30

Arg Arg Asp Phe Gly Ser Pro Xaa Glu Ala Phe Gly Gly Asn Gln Val
        35                  40                  45

Gln Lys Ala Gln Ala Met Ala Leu Val His Glu Met Leu Gln Gln Thr
    50                  55                  60

Phe Gln Leu Phe Ser Thr Glu Gly Ser Ala Ala Trp Asn Glu Ser
65                  70                  75                  80

Leu Leu His Gln Phe Tyr Thr Gly Leu Asp Gln Gln Leu Arg Asp Leu
                85                  90                  95

Glu Ala Cys Val Met Gln Glu Ala Gly Leu Glu Gly Thr Pro Leu Leu
            100                 105                 110

Glu Glu Asp Ser Ile Arg Ala Val Arg Lys Tyr Phe His Arg Leu Thr
            115                 120                 125

Leu Tyr Leu Gln Glu Lys Ser Tyr Ser Pro Cys Ala Trp Glu Ile Val
    130                 135                 140

Arg Ala Glu Val Met Arg Ser Phe Ser Ser Ser Arg Asn Leu Gln Asp
145                 150                 155                 160

Arg Leu Arg Lys Lys Glu
                165

<210> SEQ ID NO 24
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (108)..(108)
<223> OTHER INFORMATION: para-acetyl-phenylalanine (pAF)

<400> SEQUENCE: 24

Ser Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
            20                  25                  30

His Arg Arg Asp Phe Gly Ser Pro His Glu Ala Phe Gly Gly Asn Gln
        35                  40                  45

Val Gln Lys Ala Gln Ala Met Ala Leu Val His Glu Met Leu Gln Gln
    50                  55                  60

Thr Phe Gln Leu Phe Ser Thr Glu Gly Ser Ala Ala Ala Trp Asn Glu
65                  70                  75                  80

Ser Leu Leu His Gln Phe Tyr Thr Gly Leu Asp Gln Gln Leu Arg Asp
                85                  90                  95

Leu Glu Ala Cys Val Met Gln Glu Ala Gly Leu Xaa Gly Thr Pro Leu
            100                 105                 110

Leu Glu Glu Asp Ser Ile Arg Ala Val Arg Lys Tyr Phe His Arg Leu
            115                 120                 125

Thr Leu Tyr Leu Gln Glu Lys Ser Tyr Ser Pro Cys Ala Trp Glu Ile
    130                 135                 140

Val Arg Ala Glu Val Met Arg Ser Phe Ser Ser Ser Arg Asn Leu Gln
145                 150                 155                 160

Asp Arg Leu Arg Lys Lys Glu
                165

<210> SEQ ID NO 25
<211> LENGTH: 168
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (109)..(109)
<223> OTHER INFORMATION: para-acetyl-phenylalanine (pAF)

<400> SEQUENCE: 25

Ser Gly Cys Asp Leu Pro Gln Thr His Ser Leu Ala His Thr Arg Ala
1               5                   10                  15

Leu Arg Leu Leu Ala Gln Met Arg Arg Ile Ser Pro Phe Ser Cys Leu
            20                  25                  30

Asp His Arg Arg Asp Phe Gly Ser Pro His Glu Ala Phe Gly Gly Asn
            35                  40                  45

Gln Val Gln Lys Ala Gln Ala Met Ala Leu Val His Glu Met Leu Gln
 50                  55                  60

Gln Thr Phe Gln Leu Phe Ser Thr Glu Gly Ser Ala Ala Ala Trp Asn
65                  70                  75                  80

Glu Ser Leu Leu His Gln Phe Tyr Thr Gly Leu Asp Gln Gln Leu Arg
                85                  90                  95

Asp Leu Glu Ala Cys Val Met Gln Ala Gly Leu Xaa Gly Thr Pro
            100                 105                 110

Leu Leu Glu Glu Asp Ser Ile Arg Ala Val Arg Lys Tyr Phe His Arg
            115                 120                 125

Leu Thr Leu Tyr Leu Gln Glu Lys Ser Tyr Ser Pro Cys Ala Trp Glu
            130                 135                 140

Ile Val Arg Ala Glu Val Met Arg Ser Phe Ser Ser Arg Asn Leu
145                 150                 155                 160

Gln Asp Arg Leu Arg Lys Lys Glu
                165

<210> SEQ ID NO 26
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (108)..(108)
<223> OTHER INFORMATION: para-acetyl-phenylalanine (pAF)

<400> SEQUENCE: 26

His Cys Asp Leu Pro Gln Thr His Ser Leu Ala His Thr Arg Ala Leu
1               5                   10                  15

Arg Leu Leu Ala Gln Met Arg Arg Ile Ser Pro Phe Ser Cys Leu Asp
            20                  25                  30

His Arg Arg Asp Phe Gly Ser Pro His Glu Ala Phe Gly Gly Asn Gln
            35                  40                  45

Val Gln Lys Ala Gln Ala Met Ala Leu Val His Glu Met Leu Gln Gln
 50                  55                  60

Thr Phe Gln Leu Phe Ser Thr Glu Gly Ser Ala Ala Ala Trp Asn Glu
65                  70                  75                  80

Ser Leu Leu His Gln Phe Tyr Thr Gly Leu Asp Gln Gln Leu Arg Asp
                85                  90                  95

Leu Glu Ala Cys Val Met Gln Ala Gly Leu Xaa Gly Thr Pro Leu
            100                 105                 110

Leu Glu Glu Asp Ser Ile Arg Ala Val Arg Lys Tyr Phe His Arg Leu
            115                 120                 125

Thr Leu Tyr Leu Gln Glu Lys Ser Tyr Ser Pro Cys Ala Trp Glu Ile
            130                 135                 140

Val Arg Ala Glu Val Met Arg Ser Phe Ser Ser Arg Asn Leu Gln
145                 150                 155                 160

Asp Arg Leu Arg Lys Lys Glu
                165

What is claimed is:

1. A porcine interferon-α (pIFN-α) variant comprising:

(SEQ ID NO: 1)
X$_a$X$_b$CDLPQTHSLAHTRALRLLAQMRRISPFSCLDHRRDFGSPHEAFGGN

QVQKAQAMALVHEMLQQTFQLFSTEGSAAAWNESLLHQFYTGLDQQLRDL

EACVMQEAGLEGTPLLEEDSIRAVRKYFHRLTLYLQEKSYSPCAWEIVRA

EVMRSFSSSRNLQDRLRKKE, wherein residue E103, E107, L112, Y136, or Q102 (numbering with respect to SEQ ID NO: 4) is substituted with a synthetic amino acid; and wherein X$_a$X$_b$ are variable positions selected from the group consisting of no amino acids, a single proline residue, and a proline-serine dipeptide.

2. The pIFN-α variant of claim 1, wherein the synthetic amino acid is para-acetyl-phenylalanine (pAF).

3. The pIFN-α variant of claim 1, wherein the variant is selected from the group consisting of SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 17, SEQ ID NO: 19, and SEQ ID NO: 20.

4. The pIFN-α variant of claim 1, wherein the synthetic amino acid is pegylated.

5. The pIFN-α variant of claim 4, wherein the pegylated pIFN-α variant is pegylated with about a 5 kDa to 40 kDa PEG.

6. The pIFN-α variant of claim 5, wherein the PEG is a 30 kDa PEG.

7. The pIFN-α variant of claim 1 in a formulation comprising 20 mM sodium acetate, 100 mM sodium chloride, 5% glycerol at pH 5.0 of about 2.0 to about 6.0 g/L titer of pIFN-α variant.

8. A porcine interferon-α (pIFN-α) variant consisting of:

(SEQ ID NO: 14)
PSCDLPQTHSLAHTRALRLLAQMRRISPFSCLDHRRDFGSPHEAFGGNQV

QKAQAMALVHEMLQQTFQLFSTEGSAAAWNESLLHQFYTGLDQQLRDLEA

CVMQEAGL-pAF-GTPLLEEDSIRAVRKYFHRLTLYLQEKSYSPCAWEIV

RAEVMRSFSSSRNLQDRLRKKE, wherein a residue corresponding to E107 (numbering with respect to SEQ ID NO: 4) is substituted with para-acetyl-phenylalanine (pAF) and said pAF residue is pegylated with a 30 kDa linear PEG.

9. A method of treating a virus infection in a pig comprising administering subcutaneously to said pig in need thereof a pIFN-α variant; wherein the pIFN-α variant is selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

10. The method of claim 9, wherein the pIFN-α variant is administered in the range of 25 µg/kg to 150 µg/kg animal weight.

11. The method of claim 10, comprising a second administration of 25 µg/kg to 150 µg/kg animal weight of said pIFN-α variant.

12. The method of claim 11, wherein the second administration is 7 to 14 days after first administration.

13. The method of claim 9, wherein the virus infection is selected from the group consisting of: porcine reproductive and respiratory syndrome virus, foot and mouth disease virus, swine influenza virus, porcine circovirus, porcine epidemic diarrhea virus and transmissible gastroenteritis virus.

14. The method of claim 9, wherein the pig is a newborn pig or the pig is a pregnant pig.

* * * * *